US012557999B2

(12) United States Patent
Ferris et al.

(10) Patent No.: US 12,557,999 B2
(45) Date of Patent: Feb. 24, 2026

(54) QUANTITATIVE MEASUREMENT OF DISRUPTIONS IN THE BLOOD BRAIN BARRIER

(71) Applicant: Northeastern University, Boston, MA (US)

(72) Inventors: Craig Ferris, Holden, MA (US); Ju Qiao, Boston, MA (US); Praveen Kulkarni, East Walpole, MA (US); Codi Gharagouzloo, Carlisle, PA (US)

(73) Assignee: Northeastern University, Boston, MA (US)

( * ) Notice: Subject to any disclaimer, the term of this patent is extended or adjusted under 35 U.S.C. 154(b) by 627 days.

(21) Appl. No.: 17/420,202

(22) PCT Filed: Jan. 3, 2020

(86) PCT No.: PCT/US2020/012191
§ 371 (c)(1),
(2) Date: Jul. 1, 2021

(87) PCT Pub. No.: WO2020/142696
PCT Pub. Date: Jul. 9, 2020

(65) Prior Publication Data
US 2022/0087562 A1     Mar. 24, 2022

Related U.S. Application Data

(60) Provisional application No. 62/787,819, filed on Jan. 3, 2019.

(51) Int. Cl.
*A61B 5/055* (2006.01)
*G01R 33/56* (2006.01)
(52) U.S. Cl.
CPC .......... *A61B 5/055* (2013.01); *G01R 33/5601* (2013.01); *G06T 2207/10088* (2013.01)

(58) Field of Classification Search
CPC ................ A61B 5/055; G01R 33/5601; G01R 33/4816; G06T 2207/10088; G06T 2207/10092; G06T 2207/10096
See application file for complete search history.

(56) References Cited

U.S. PATENT DOCUMENTS 7,788,722 B1     8/2010     Njemanze et al.
7,962,960 B2     6/2011     Fudge
(Continued)

FOREIGN PATENT DOCUMENTS

CN     102548571 A     7/2012
RU     2315559 C1     1/2008
(Continued)

OTHER PUBLICATIONS

"Feraheme (ferumoxytol) injection label", from https://www.accessdata.fda.gov/drugsatfda_docs/label/2009/022180lbl.pdf. Available at least since Feb. 16, 2017 (See https://web.archive.org/web/20170216125428/https://www.accessdata.fda.gov/drugsatfda_docs/label/2009/022180lbl.pdf) (Year: 2017).*
(Continued)

*Primary Examiner* — Keith M Raymond
*Assistant Examiner* — Milton Truong
(74) *Attorney, Agent, or Firm* — Foley Hoag LLP; Dana M. Gordon; Laura A. Wzorek

(57) ABSTRACT

Disclosed are methods for determining blood brain barrier disruption in a subject in need thereof. The methods include administering intravascularly a contrast agent to the subject; performing quantitative ultra-short time-to-echo contrast-enhanced magnetic resonance imaging (QUTE-CE MRI) on a region of interest of the subject's brain; and determining presence of the contrast agent in brain parenchyma and/or cerebral spinal fluid within the region of interest.

21 Claims, 14 Drawing Sheets

(56) References Cited

U.S. PATENT DOCUMENTS

| | | | |
|---|---|---|---|
| 8,201,257 | B1 | 6/2012 | Andres et al. |
| 9,274,193 | B2 | 3/2016 | Johnson |
| 10,338,180 | B2 | 7/2019 | McMillan et al. |
| 2001/0031242 | A1 | 10/2001 | Cremillieux et al. |
| 2002/0147803 | A1 | 10/2002 | Dodd et al. |
| 2005/0215881 | A1 | 9/2005 | Van Zijl et al. |
| 2007/0080685 | A1 | 4/2007 | Bydder et al. |
| 2009/0246145 | A1 | 10/2009 | Small |
| 2009/0264733 | A1 | 10/2009 | Corum et al. |
| 2010/0129292 | A1 | 5/2010 | Jerosch-Herold et al. |
| 2012/0092010 | A1 | 4/2012 | Corum et al. |
| 2012/0150048 | A1 | 6/2012 | Kang et al. |
| 2012/0179028 | A1 | 7/2012 | Caravan et al. |
| 2012/0268122 | A1 | 10/2012 | Carl |
| 2012/0289511 | A1 | 11/2012 | Alam |
| 2014/0084919 | A1 | 3/2014 | Johnson |
| 2015/0065865 | A1 | 3/2015 | Leigh et al. |
| 2016/0000945 | A1 | 1/2016 | Nedergaard et al. |
| 2017/0079581 | A1* | 3/2017 | Walczak ............... A61K 47/26 |
| 2017/0102439 | A1 | 4/2017 | McMillan et al. |
| 2019/0180139 | A1* | 6/2019 | Zach ................... A61B 5/0042 |
| 2019/0246938 | A1 | 8/2019 | Gharagouzloo et al. |
| 2019/0247662 | A1 | 8/2019 | Poltroak |
| 2020/0051246 | A1* | 2/2020 | Carmi ................... A61B 5/055 |
| 2021/0298662 | A1 | 9/2021 | Gharagouzloo et al. |
| 2022/0087562 | A1 | 3/2022 | Ferris et al. |
| 2022/0110524 | A1 | 4/2022 | Ferris et al. |

FOREIGN PATENT DOCUMENTS

| | | | | |
|---|---|---|---|---|
| WO | WO-2017019182 | A1 * | 2/2017 | ............. A61B 5/055 |
| WO | WO-2018/094076 | A1 | 5/2018 | |
| WO | WO-2020/023980 | A1 | 1/2020 | |
| WO | WO-2020/142696 | A1 | 7/2020 | |
| WO | WO-2020/154732 | A1 | 7/2020 | |

OTHER PUBLICATIONS

Xu, X. et al. "Dynamic Glucose Enhanced (DGE) MRI for Combined Imaging of Blood-Brain Barrier Break Down and Increased Blood Volume in Brain Cancer." Magnetic Resonance in Medicine 74:1556-1563 (2015) (Year: 2015).*

Shah, M. et al. "Evaluating intensity normalization on MRIs of human brain with multiple sclerosis." Medical Image Analysis 15: 267-282 (2011) (Year: 2011).*

Perles-Barbacaru, A.T. et al. "A new Magnetic Resonance Imaging method for mapping the cerebral blood volume fraction: the rapid steady-state T1 method." Journal of Cerebral Blood Flow & Metabolism 27: 618-631 (2007) (Year: 2007).*

Wardlaw, J.M. et al. "Changes in Background Blood-Brain Barrier Integrity Between Lacunar and Cortical Ischemic Stroke Subtypes". Stroke 39(4):1327-32 (2008) (Year: 2008).*

Heye, A.K. et al. "Tracer kinetic modelling for DCE-MRI quantification of subtle blood-brain barrier permeability". NeuroImage 125 446-455 (2016) (Year: 2016).*

International Search Report and Written Opinion for International Application No. PCT/US2020/012191 mailed Mar. 19, 2020.

Morrison et al., "Early Detection of Cerebral Microbleeds Following Mild Traumatic Brain Injury Using QUTE-CE MRI," Presented Nov. 7, 2018 at the Society for Neuroscience Meeting, San Diego, CA.

Bilston et al., "Arterial Pulsation-driven Cerebrospinal Fluid Flow in the Perivascular Space: A Computational Model," Computer Methods in Biomechanics and Biomedical Engineering, 6(4): 235-241 (2003).

International Search Report and Written Opinion for International Application No. PCT/US2020/015223 dated Apr. 6, 2020.

Lam et al., "The ultrastructure of spinal cord perivascular spaces: Implications for the circulation of cerebrospinal fluid," Scientific Reports, 7: 12924 (2017).

Lliff et al., "A Paravascular Pathway Facilitates CSF Flow Through the Brain Parenchyma and the Clearance of Interstitial Solutes, Including Amyloid β," Sci Transl Med., 4(147): 147ra111 (2012).

Rennels et al., "Evidence for a 'Paravascular' Fluid Circulation in the Mammalian Central Nervous System, Provided by the Rapid Distribution of Tracer Protein Throughout the Brain from the Subarachnoid Space," Brain Research, 326: 47-63 (1985).

Taoka et al., "Gadolinium-based Contrast Media, Cerebrospinal Fluid and the Glymphatic System: Possible Mechanisms for the Deposition of Gadolinium in the Brain," Magnetic Resonance in Medical Sciences, 17(2):111-119 (2018).

Arai et al., "Brain angiogenesis in developmental and pathological processes: neurovascular injury and angiogenic recovery after stroke", FEBS J. vol. 276, No. 17, pp. 4644-4652, (2009).

Assini et al., "Object location memory in mice: Pharmacological validation and further evidence of hippocampal CA1 participation", Behav Brain Res. vol. 204, No. 1, pp. 206-211, (2009).

Bane, et al., "Leakage and Water Exchange Characterization of Gadofosveset in the Myocardium", Magnetic Resonance Imaging, vol. 32, No. 3, pp. 224-235, Apr. 2014.

Banerjee et al., "Novel imaging techniques in cerebral small vessel diseases and vascular cognitive impairment", Biochim. Biophys. Acta—Mot Basis Dis. 1862, pp. 926-938, (2015).

Barbier et al., "Methodology of Brain Perfusion Imaging", Journal of Magnetic Resonance Imaging, vol. 13, pp. 496-520, (2001).

Barker et al., "Relative Frequencies of Alzheimer Disease, Lewy Body, Vascular and Frontotemporal Dementia, and Hippocampal Sclerosis in the State of Florida Brain Bank", Alzheimer Dis Assoc Disord., vol. 16, No. 4, pp. 203-212, (2002).

Bremerich et al., "MR angiography with blood pool contrast agents", Eur Radial. vol. 17, No. 12, pp. 3017-3024, (2007).

Brookheimer et al., "Patterns of brain activation in people at risk for Alzheimer's disease", N Engl J Med., vol. 343, No. 7, pp. 450-456, (2000).

Brunser et al., "Accuracy of diffusion-weighted imaging in the diagnosis of stroke in patients with suspected cerebral infarct", Stroke, pp. 1169-1171, (2013).

Charidimou et al., "Sporadic cerebral amyloid angiopathy revisited: Recent insights into pathophysiology and clinica spectrum", J Neural Neurosurg Psychiatry., vol. 83, No. 2, pp. 124-137, (2012).

Chen et al., "Neurovascular abnormalities in brain disorders: highlights with angiogenesis and magnetic resonance imaging studies", J. Biomed Sci., vol. 20, pp. 1-8, (2013).

Christen et al., "High-resolution cerebral blood volume imaging in humans using the blood pool contrast agent erumoxytol", Magn Reson Med., vol. 70, No. 3, pp. 705-710, Sep. 2013.

Cunningham et al., "Positive contrast magnetic resonance imaging of cells labeled with magnetic nanoparticles", Magn Reson Med., vol. 53, No. 5, pp. 999-1005, May 2005.

Desai et al., "Evidence of angiogenic vessels in Alzheimer's disease", J Neural Transm., vol. 116, pp. 587-597, May 2009.

Du et al., Qualitative and quantitative ultrashort-TE MRI of cortical bone, NMR Biomed., vol. 26, No. 5, pp. 489-506, May 2013.

Filippini et al., "Distinct patterns of brain activity in young carriers of the APOE-?4 allele", Proc Natl Acad Sci., vol. 106, No. 17, pp. 7209-7214, (2009).

Forshult, "Magnetic Resonance Imaging MRI—An Overview", Karlstad, Sweden: Karlstad University (2007), p. 9.

Gharagouzloo et al., "Central Nervous System Diagnostics with QUTE-CE", Poster presented at Northeastern's University ITNANO Presentation, 1 page (2014).

Gharagouzloo et al., "Diagnosing Neuropathey Early with QUTE-CE MRI", Poster presented at IGERT Illanomedicine 1st Annual Nanomedicine Day, 1 page (2015).

Gharagouzloo et al., "ISMRM Abstract", ISMRM Abstract submitted and poster presented at ISMRM, 1 page (2014).

Gharagouzloo et al, "Longitudinal Monitoring of Nanoparticle Accumulation in PC-3 Tumors", Poster presented at Northeastern University Research, Innovation and Scholarship Expo, 1 page (2015).

Gharagouzloo et al, "Positive Contrast Ultrashort TE imaging with Ferumoxytol Contrast Agent". Poster presented at NCIGT Workshop, 2012, 1 page.

(56)                    References Cited

OTHER PUBLICATIONS

Gharagouzloo et al, "Quantitative Imaging of Magnetic Nanoparticles in Mouse Vasculature", Poster presented at IGERT Nanomedicine 1st Annual Nanomedicine Day, 1 page (2015).

Gharagouzloo et al, "Quantitative Positive Contrast MRI with Iron Oxide Nanoparticles". Poster presented at Northeastern University ITNANO Presentation, 1 page (2013).

Gharagouzloo et al, "Quantitative ultra-high resolution MR imaging using magnetic nanoparticles", Poster presented at NCIGT Workshop, 1 page (2014).

Gharagouzloo et al., "Ultra-short TE imaging with SPIONs—Bright prospects for in vivo applications.", Abstract presented at Northeastern University Research, Innovation and Scholarship Expo, 1 page (2013).

Gharagouzloo et al, "Ultrashort TE imaging with SPIONs: bright prospects for in vivo applications", AACR/SNMMI State-of-the-Art Molecular Imaging in Cancer Biology and Therapy: Abstracts, Molecular Imaging in Cancer, Abstract No. 28, p. 9, 2013, total 36 pages.

Gharagouzloo et al, "UTE Angiograpy with ferumoxytol", Abstract Published at IEEE NEBEC, retrieved from eeexplore.ieee.org/document/6972796; 2 pages (2014).

Gharagouzloo et al., "Contrast Enhanced Quantitative UTE (QUTE-CE) MRI for Cerebral Blood Imaging and Cancer Diagnostics", RISE 2014, Abstract ID# 301, Northeastern University, Apr. 10, 2014.

Gharagouzloo et al., "Environment and mobility influence on magnetic nanoparticles with Ferumoxytol", Poster ; presented at World Molecular Imaging Congress, 1 page (2012).

Gharagouzloo et al., "Functional neuroimaging using dynamic radial 3D UTE pulse sequences", Poster presented at ISMRM, 1 page (2017).

Gharagouzloo et al., "Quantitative In Vivo Concentration Determination of Magnetic Nanoplatforms with Ultra-Short TE Magnetic Resonance Imaging UTE", Poster presented at First International Translational Nanomedicine Conference, Boston, MA,, 1 page (2013).

Gharagouzloo et al., "Quantitative vascular measurements in ApoE-E:-4 knock-in female rats before onset of AD", International Society for Magnetic Resonance in Medicine, ISMRM, 2030 Addison Street, 7th Floor, Berkeley, CA 94704 USA, No. , Jun. 1, 2018, XP040701222, 3 pages (2014).

Gharagouzloo et al., "Quantitative vascular neuroimaging of the rat brain using superparamagnetic nanoparticles: New insights on vascular organization and brain function", Neuroimage.; 163:24-33. doi: 10.1016/j.neuroimage. 21 pages (2017).

Gharagouzloo, C.A. et al, "Quantitative Contrast-Enhanced MRI with Superparamagnetic Nanoparticles Using Ultrashort Time-to-Echo Pulse Sequences", Magnetic Resonance Imaging, vol. 74, No. 2, 431-441; EPub; Aug. 28 (online) DOI: 10.1002/mrm.25426 (2015).

Gorelick et al., Vascular contributions to cognitive impairment and dementia: A statement for healthcare professionals from the American Heart Association/American Stroke Association, Stroke, vol. 42, No. 9, pp. 2672-2713, (2011).

Greenberg et al., "Cerebral microbleeds: a guide to detection and interpretation", Lancet Neural., 19 pages (2009).

Guo et al., "The Vasculome of the Mouse Brain", PLoS One. vol. 7, 17 pages (2012).

Gupta et al., "Impaired Aß clearance: A potential link between atherosclerosis and Alzheimer's disease", Front Aging Neurosci., 8 pages (2015).

Hachinski, V., "Dementia: Paradigm shifting into high gear", Alzheimers Dement., vol. 15, No. 7, pp. 985-994, Jul. 2019.

Iadecola, "The Pathobiology of Vascular Dementia", Neuron., vol. 80, No. 4, pp. 844-866, (2013).

Jack et al., "Serial PIB and MRI in normal, mild cognitive impairment and Alzheimers disease: Implications for sequence of pathological events in Alzheimers disease", Brain, vol. 132, No. 5, pp. 1355-1365, (2009).

Johnson et al., "Hybrid Radial-Cones Trajectory for Accelerated Magnetic Resonance Imaging", Magn Reson Med., vol. 77, No. 3, pp. 1068-1081, Mar. 2017.

Kim et al., In Vivo Quantification of Transvascular Water Exchange During the Acute Phase of Permanent Stroke, Magn Reson Med., vol. 60, No. 4, pp. 813-821, Oct. 2008.

Kim, S. et al., "Cerebral Blood Volume MRI with Intravascular Superparamagentic Iron Oxide Nanoparticles", NMR Biomedicine, vol. 26, No. 8, pp. 949-962, Aug. 2012.

Kwon et al., "Simultaneous evaluation of vascular morphology, blood volume and transvascular permeability using SPION-based, dual-contrast MRI: imaging optimization and feasibility test", NMR In Biomedicine, vol. 28, pp. 624-632, (2015).

Kwong et al., "Dynamic magnetic resonance imaging of human brain activity during primary sensory stimulation", Proc Natl Acad Sci USA, vol. 89, No. 12, pp. 5675-5679, (1992).

Leaston et al., "Neurovascular imaging with QUTE-CE MRI in APOE4 rats reveals early vascular abnormalities", PLOS One Aug. 27, 16 pages (2021).

Li et al., "Angiogenesis and improved cerebral blood flow in the ischemic boundary area detected by MRI after :idministration of sildenafil to rats with embolic stroke", Brain Res., vol. 1132, No. 1, pp. 185-192, (2007).

Mandeville, "Iron fMRI measurements of CBV and implications for BOLD signal", Neuroimage, vol. 62, No. 2, pp. 1000-1008, (2012).

Marques et al., "Low-Field MRI: An MR Physics Perspective," Journal of Magnetic Resonance Imaging, vol. 49, No. 6, pp. 1528-1549, (2019).

Murase, "Generalized equation for describing the magnetization in spoiled gradient-echo imaging", Magnetic Resonance Imaging, vol. 29, No. 5, pp. 723-730, Jun. 2011.

Reijmer et al., "Ischemic brain injury in cerebral amyloid angiopathy", J Cereb Blood Flow Metab, 15 pages (2016).

Reiman et al., "Brain imaging and fluid biomarker analysis in young adults at genetic risk for autosomal dominant Alzheimer's disease in the presenilin 1 E280A kindred: A case-control study", Lancet Neurol., vol. 11, No. 12, pp. 1048-1056, (2012).

Rohrer et al., "Comparison of Magnetic Properties of MRI Contrast Media Solutions at Different Magnetic Field Strengths, Investigative Radiology", vol. 40, No. 11, pp. 715-724, Nov. 2005.

Schabel et al., "Uncertainty and bias in contrast concentration measurements using spoiled gradient echo pulse ,equences", Phys Med Biol., vol. 53, No. 9, pp. 2345-2373, (2008).

Schild, H.H., "MRI made easy( . . . well almost)", Berlin: Schering AG, p. 96 (1990).

Seevinck et al., "Magnetic resonance imaging of brain angiogenesis after stroke", Angiogenesis, vol. 13, No. 2, pp. 101-111, (2010).

Semple et al., "Brain development in rodents and humans: Identifying benchmarks of maturation and vulnerability to injury across species", Prog Neurobiol., vol. 106, pp. 1-16, Jul. 2013.

Shi et al., "Update on cerebral small vessel disease: a dynamic whole-brain disease", BMJ, vol. 1, No. 3, pp. 83-92, (2016).

Stuber et al., "Positive contrast visualization of iron oxide-labeled stem cells using inversion-recovery with ON-resonant water suppression (IRON)", Magn Reson Med., vol. 58, pp. 1072-1077, (2007).

Sutphin et al. "Male Pelvic MR Angiography", Magnetic Resonance Imaging Cln. N. Am. vol. 22, No. 2, May 2014.

Tropres et al., Vessel size imaging, Magn Reson Med., vol. 45, pp. 397-408, (2001).

Uh et al., "Cerebral blood volume in Alzheimer's disease and correlation with tissue structural integrity", Neurobiology of Aging, vol. 31, No. 12, pp. 2038-2046, (2010).

Walker-Samuel et al., "Reference tissue quantification of DCE-MRI data without a contrast agent calibration", Phys Med Biol., vol. 52, No., 3, pp. 589-601, Jan. 2007.

Wang et al., "Improving detection specificity of iron oxide nanoparticles (ION Ps) using the SWIFT sequence with long T2 suppression", Magn Reson Imaging, vol. 32, No. 6, pp. 671-678, Jul. 1, 2014.

Wardlaw et al., "Mechanisms underlying sporadic cerebral small vessel disease: insights from neuroimaging", Lancet Neurol., vol. 12, No. 5, pp. 1-27, (2013).

(56) References Cited

OTHER PUBLICATIONS

Wardlaw et al., "Neuroimaging standards for research into small vessel disease and its contribution to ageing and 11eurodegeneration", Lancet Neurol., vol. 12, No. 8, pp. 822-838, (2013).

Wey et al., "A review of current imaging methods used in stroke research", Neurol Res., vol. 35, No. 10, pp. 1092-1102, Dec. 2013.

Yankeelov et al., "Dynamic Contrast Enhanced Magnetic Resonance Imaging in Oncology: Theory, Data Acquisition, Analysis and Examples", Curr Med Imaging Rev., vol. 3, No. 2, pp. 91-107, 2009.

Zhang et al., "T1-Weighted Ultrashort Echo Time Method for Positive Contrast Imaging of Magnetic Nanoparticles and Cancer Cells Bound With the Targeted Nanoparticles", J Magn Reson Imaging, vol. 33, No. 1, pp. 194-202, Jan. 2011.

Zlokovic, "Neurovascular pathways to neurodegeneration in Alzheimer's disease and other disorders", Nat. Rev Neurosci., vol. 12, No. 12, pp. 723-738, Dec. 2011.

U.S. Appl. No. 17/425,123, Pending.

* cited by examiner

QUANTITATIVE MEASUREMENT OF DISRUPTIONS IN THE BLOOD BRAIN BARRIER

RELATED APPLICATIONS

This application is a U.S. National Stage Application of International Application No. PCT/US20/12191, filed Jan. 3, 2020; which claims the benefit of priority to U.S. Provisional Patent Application No. 62/787,819, filed Jan. 3, 2019.

BACKGROUND

The blood brain barrier (BBB) is known to be disrupted in traumatic brain injury (TBI) and all major central nervous system (CNS) disorders, however no technology exists to measure the global quantitative extent of this burden. The use of molecular contrast agents (CAs), such as gadolinium-based contrast agents (GBCAs), in combination with standard magnetic resonance imaging (MM) acquisition techniques, has produced no reliable measurement of BBB disruption.

A quantitative measure of a mild TBI has evaded research and commercial applications since the onset of CNS imaging. Previous efforts to use MRI to produce reproducible biomarkers for mild TBI have proven ineffective. TBI is one of the most prevalent risks of death and disability in young people, with about 1.6 million reported per year in the US. Mild TBI (mTBI) is characterized as a negligible loss of consciousness with minimal neuropathology, and is estimated to account for 70-90% of all TBI cases. Some of the most devastating injuries from brain trauma are the rupturing of arteries between the dura and the skull in an epidural hematoma, as well as tears in emissary veins, resulting in hemorrhagic contusions seen in subdural hematomas. This accumulation of blood can squeeze and increase pressure on the brain. Microvessel disruption plays substantial role in primary, secondary and chronic effects of TBI, and understanding the response of the vascular system following traumatic brain injury is critical to our ability to effectively treat brain trauma.

Vascular dementia is a serious consequence of diabetes (Pasquir et al., 2006). Prolonged exposure to high blood levels of glucose, typical of type 2 diabetes, affects capillary endothelial structure, function and permeability (Allen et al., 2009). Failure in the blood brain barrier lies at the foundation of cerebral small vessel disease and contributes to the pathogenesis of diabetic encephalopathy (Bogush et al., 2017). Imaging the subtle changes in blood brain permeability is not possible with standard clinical imaging protocols but can be assessed with dynamic contrast enhanced (DCE) MRI (Starr et al., 2003). However, DCE MRI has several limitations. The concentration versus time curve for GBCAs is typically 15-30% inaccurate and is required for accurate measurement; therefore, DCE MRI has not proven useful clinically (Raja et al., 2018). It is also difficult to model the effects of contrast agent on both T2* and T1 given the short acquisition time, and strong dependence on microstructural properties such as vessel size, tortuosity and orientation. These and other methodological issues with the use of DCE-MRI for BBB permeability have resulted in significant differences in the reported rates of leakage (Raja et al., 2018).

There is a need for methods that allow determining BBB disruption, including methods that allow for in vivo quantification and localization of changes in blood brain barrier permeability.

SUMMARY

Methods for determining BBB disruption are disclosed. Determining BBB disruption according to the methods disclosed herein can, for example, facilitate understanding the response of the vascular system following TBI, which is critical for being able to effectively treat brain trauma, or facilitate understanding and diagnosis of early onset of vascular dementia with type 2 diabetes.

One embodiment is a method for determining blood brain barrier disruption, comprising: administering intravascularly a contrast agent to a subject in need thereof; performing quantitative ultra-short time-to-echo contrast-enhanced magnetic resonance imaging (QUTE-CE MM) on a region of interest of the subject's brain; and determining presence of the contrast agent in brain parenchyma or cerebral spinal fluid within the region of interest.

In some embodiments, performing QUTE-CE MRI provides a quantitative signal intensity which is used to determine blood brain barrier disruption by measuring 1) an increasing signal intensity post-contrast in the region of interest, 2) an apparently increasing CBV, or 3) an increased signal intensity resulting from accumulation of the contrast agent in the parenchyma or cerebral spinal fluid after the contrast agent has left the subject's blood.

In some embodiments, performing QUTE-CE MRI comprises applying a magnetic field to region of interest; applying a radio frequency pulse sequence with a selected repetition time (TR) and flip angle (FA) to excite protons in the region of interest, wherein the TR is less than about 10 ms, and the FA ranges from about 10° to about 30°; measuring a response signal during relaxation of the protons at a selected time-to-echo (TE) with magnetic field gradients activated to provide a T1-weighted signal from the region of interest, wherein the TE is an ultra-short time-to-echo (UTE) less than about 300 µs; and generating an image of the region of interest.

In some embodiments, the acquired signal is representative of a concentration of the CA in the region of interest.

In some embodiments, the methods disclosed herein further comprise setting the time to echo (TE) to less than 30 µs.

In some embodiments, the TR is set to a value below about 5 ms, the TE is set to a UTE value and the FA is selected to be around the Ernst angle of the contrast-enhanced blood.

In some embodiments, the methods disclosed herein further comprise setting the TE to zero using a Zero TE (ZTE) sequence.

In some embodiments, the methods disclosed herein further comprise setting the repetition time (TR) to a value from about 2 to about 10 ms.

In some embodiments, the methods disclosed herein further comprise setting the flip angle to a value from about 10° to about 25°.

In some embodiments, QUTE-CE MM is performed before accumulation of the CA in the brain parenchyma and/or (CSF) and is subsequently performed after administration of the CA.

In some embodiments, QUTE-CE MRI is performed before intravascular administration of the ferumoxytol.

In some embodiments, QUTE-CE MM is performed on the region of interest at a time when the CA has cleared from the subject's vascular system.

In some embodiments, the region of interest is subject's entire brain.

In some embodiments, the CA is ferumoxytol.

In aspects of these embodiments, ferumoxytol is administered in a dose to produce a starting blood concentration of between about 20 and about 200 µg/mL Fe.

In further aspects of these embodiments, ferumoxytol is administered in a dose to produce a starting blood concentration of between about 40 and about 150 µg/mL Fe.

In yet further aspects of these embodiments, ferumoxytol is administered at a dose of about 200 mg to about 1020 mg elemental iron.

In further aspects of these embodiments, ferumoxytol is administered at a dose of about 2 to about 14 mgFe/kg body weight.

In further aspects of these embodiments, ferumoxytol is administered at a dose of about 3 to about 4 mgFe/kg body weight.

In further aspects of these embodiments, ferumoxytol is administered at a dose of about 7-14 mg/kg bodyweight in animals or 2-7 mg/kg bodyweight in humans.

In some embodiments, the subject is a human.

In some embodiments, the subject has traumatic brain injury (TBI), type 2 diabetes, stroke, or a CNS disorder.

In some embodiments, the subject has a CNS disorder selected from amyotrophic lateral sclerosis, Huntington's disease, Alzheimer's disease or related dementia, and Parkinson's disease.

In some embodiments, the subject has an early stage CNS disorder selected from amyotrophic lateral sclerosis, Huntington's disease, Alzheimer's disease or related dementia, and Parkinson's disease.

In some embodiments, the subject has mild cognitive impairment

DETAILED DESCRIPTION

Figure 1:
FIG. 1 shows a pneumatic pressure drive that was used to reproduce 7.4, 9.3 and 11.2 m/s impact velocities described for mild, medium and severe rat head injury.
Figure 2A:
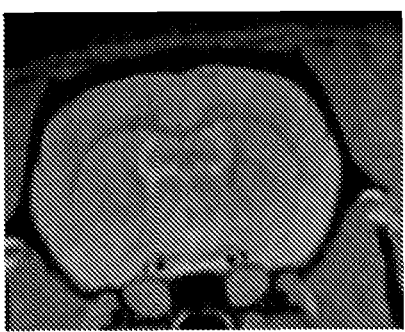
FIG. 2A shows a 2D axial T1-weighted anatomical images of a rat brain immediately after 1 hit.
Figure 2B:
FIG. 2B shows a 2D axial T1-weighted anatomical images of a rat brain immediately after 2 hits.
Figure 2C:
FIG. 2C shows a 2D axial T1-weighted anatomical images of a rat brain immediately after 3 hits.

The various concepts introduced above and discussed in greater detail below may be implemented in any of numerous ways, as the described concepts are not limited to any particular manner of implementation. Examples of specific implementations and applications are provided primarily for illustrative purposes.

Methods for determining BBB disruption are disclosed. The methods are based on the introduction of intravascular (CA) and the measurement of CA leakage into the brain parenchyma without evidence of capillary rupture. Whereas microbleeds can be found with susceptibility-weighted imaging (SWI) in major cases of TBI, no technology has proven sensitive enough to detect mTBI or to quantify the burden in major TBI. Furthermore, whereas existing techniques for BBB integrity require careful visual inspection of specific, and limited regions of the brain by a trained radiologist, the disclosed technology can give a non-biased global quantitative perspective of whole-brain changes in BBB integrity. This can be achieved by introduction of an intravascular CA and use of UTE (UTE) pulse sequences, such as with the QUTE-CE method, to generate a quantitative signal intensity, which can be followed longitudinally from the time of injection to determine if signal increases resulting from CA accumulation do occur, including measurements at a time at which CA has been entirely cleared from the blood and CA resides within in the parenchymal space beyond the BBB.

One embodiment is a method for determining blood brain barrier (BBB) disruption in a subject in need thereof, the method comprising: administering intravascularly a contrast agent (CA) to the subject; performing quantitative ultra-short time-to-echo contrast-enhanced magnetic resonance imaging (QUTE-CE MRI) on a region of interest of the subject's brain; and determining presence of the contrast agent in brain parenchyma and/or cerebral spinal fluid (CSF) within the region of interest. In an aspect of this embodiment, presence of the contrast agent is determined in brain parenchyma or cerebral spinal fluid (CSF) within the region of interest. In another aspect of this embodiments, presence of the contrast agent is determined in brain parenchyma and cerebral spinal fluid (CSF) within the region of interest. In another aspect of this embodiments, presence of the contrast agent is determined in brain parenchyma within the region of interest.

In some embodiments, performing QUTE-CE MRI provides a quantitative signal intensity which is used to determine blood brain barrier disruption by measuring 1) an increasing signal intensity post-contrast in the region of interest, 2) an apparently increasing CBV (which takes into account pre-contrast imaging and normalizes by the blood intensity using a two-volume blood/tissue model) within the region of interest, or 3) an increased signal intensity resulting from accumulation of the contrast agent in the parenchyma or cerebral spinal fluid after contrast agent has left the subject's blood.

In some embodiments, performing QUTE-CE MRI provides a quantitative signal intensity which is used to determine blood brain barrier disruption by measuring an increasing signal intensity post-contrast in the region of interest.

In some embodiments, performing QUTE-CE MRI provides a quantitative signal intensity which is used to determine blood brain barrier disruption by measuring an apparently increasing CBV within a region of interest. In an aspect of this embodiments, performing QUTE-CE MRI provides a quantitative signal intensity which is used to determine blood brain barrier disruption by measuring an apparently increasing CBV which takes into account pre-contrast imaging and normalizes by the blood intensity using a two-volume blood/tissue model.

In some embodiments, performing QUTE-CE MRI provides a quantitative signal intensity which is used to determine blood brain barrier disruption by measuring an increased signal intensity resulting from accumulation of the contrast agent in the parenchyma or cerebral spinal fluid after contrast agent (e.g., ferumoxytol) has left the subject's blood.

QUTE-CE MRI, as previously described in (Gharagouzloo et al., 2015), (Gharagouzloo et al., 2017) and (U.S. Patent Application Publication No. 2019/0246938, entitled "Quantitative Magnetic Resonance Imaging of the Vasculature"; incorporated by reference) can be used in the methods disclosed herein to obtain information representative of contrast agent (i.e., ferumoxytol) concentration in the part or all of the subject's brain. Quantitative ultra-short time-to-echo (QUTE-CE) MRI is a technique that allows producing a quantitative signal intensity for MRI. This quantitative signal intensity has been shown to be used to quantify contrast agent concentration in blood (Gharagouzloo et al., 2015) and quantify contrast-enhanced blood per voxel in the brain (Gharagouzloo et al., 2017).

In the underlying theory of QUTE-CE MRI, the intensity magnitude IM of each voxel is a function of standard MM parameters governed by the Spoiled Gradient Echo (SPGR) equation, $$I_M = Kp \cdot e^{(-TE/T_2)} \cdot \sin(FA) \frac{1 - e^{(-TR/T_1)}}{1 - e^{(-TR/T_1)} \cdot \cos(FA)}, \quad (1)$$

where TE is the time-to-echo, TR is the repetition time, and FA is the flip angle. TE, TR, and FA are user-defined image acquisition parameters. $T_1$ and $T_2$ are relaxation time constants dependent on the local environment of each voxel, which is mutable via CAs, and dependent on the magnetic field strength. K is a constant determined by the properties of the receive coil and $\rho$ is the proton density of the medium. TE is typically chosen to be <100 $\mu$s to eliminate susceptibility-induced signal modifications. The choice of a very low TR (<5 ms) with a 3D volume excitation pulse minimizes effects from the extravascular water exchange and eliminates signal enhancement from blood flow within the cranial space. This can be achieved with either hard pulse or slab-select pulse. Setting the FA at the Ernst angle maximizes the T1-enhanced signal and minimizes sensitivity to small perturbations in FA.

In some embodiments, performing QUTE-CE MRI comprises applying a magnetic field to region of interest; applying a radio frequency pulse sequence at a selected TR and at a magnetic field gradient to provide a selected FA to excite protons in the region of interest, wherein the TR is less than about 10 ms, and the FA ranges from about 10° to about 30°; measuring a response signal during relaxation of the protons at a selected TE to acquire a $T_1$-weighted signal from the region of interest, wherein the time to echo is an ultra-short time to echo less than about 300 $\mu$s; and generating an image of the region of interest.

In some embodiments, the acquired signal is representative of a concentration of the CA in the region of interest.

In some embodiments, the disclosed methods further comprise setting the TE to less than about 30 $\mu$s.

In some embodiments, the disclosed methods further comprise setting the TR to a value from about 1 to about 10 ms.

In some embodiments, the disclosed methods further comprise setting the flip angle to a value from about 10° to about 25°.

In some embodiments, QUTE-CE MRI is performed using a TE of about 13 $\mu$s, a TR of about 4 ms and an FA of about 20° with a high radio frequency (RF) pulse bandwidth of 200 kHz. This results in a pulse duration of 6.4 $\mu$s which is short compared to the $T_2$ of the approximate ferumoxytol concentration (Gharagouzloo et al., 2017). Choosing a pulse duration which is short compared to the $T_2$ of the approximate ferumoxytol concentration minimizes signal blur and reduce the probability for a curved trajectory of the magnetization vector $M_z$ (Gharagouzloo et al., 2017).

QUTE-CE MRI can be performed with commercially available magnetic resonance imaging devices, as they are found, for example, in clinical, hospital and medical laboratory settings. QUTE-CE MRI is a technique that produces a quantitative signal intensity for MRI. This quantitative signal intensity has been shown to be used to quantify contrast agent concentration in blood (Gharagouzloo et al., 2015) and quantify contrast-enhanced blood per voxel in the brain (Gharagouzloo et al., 2017).

The methods disclosed herein, include performing the QUTE-CE MM method on a region of interest of the subject's brain. A region of interest can be a part of the subject's brain or the entirety of the subject's brain, and typically is a region of the brain that is suspected or known to include BBB disruption such that CA (e.g., ferumoxytol) leaks into the brain parenchyma in the region.

After intravascular administration of CA (e.g., ferumoxytol) to the subject, it takes some time for CA to leak into parenchymal space of the brain due to BBB disruption. Accordingly, typically, a pre-contrast image of the region of interest is determined, and, subsequently, one or more images are acquired to determine a baseline (i.e., before much ferumoxytol has been able to accumulate in the parenchymal space, e.g., shortly after ferumoxytol has reached a steady-state blood concentration), subsequently, one more images are acquired to determine ferumoxytol concentration in the parenchymal space of the region of interest of the subject's brain wherein the signal intensity in post-contrast images increases over time as CA leaks out of the vascular space.

In some embodiments, the methods disclosed herein, include calculating quantitative cerebral blood volume (CBV) (provided in (Gharagouzloo et al., 2017)), and increasing CBV, instead of signal intensity, can be used to determine BBB disruption.

In some embodiments, QUTE-CE MRI is performed before accumulation of the CA in the brain parenchyma and is subsequently performed after administration of the CA.

In some embodiments, QUTE-CE MM is performed before intravascular administration of the CA, e.g., ferumoxytol.

In some embodiments, the methods disclosed herein comprise performing QUTE-CE MM on the region of interest at a time when the CA has cleared from the subject's vascular system.

Further information regarding performing the QUTE-CE MM method, including preparing a brain atlas containing a plurality of anatomical and functional regions, obtaining a high-resolution anatomical data set of the region of interest, and image processing are provided in (Gharagouzloo et al., 2017). The methods described herein can include imaging the region of interest with voxels registered to a brain atlas providing site-specific information on BBB permeability in different brain areas within the region of interest.

The methods disclosed herein include administration of a CA. Suitable CAs leak into the brain's parenchyma when the BBB is disrupted.

In some embodiments, the CA is ferumoxytol. Ferumoxytol is an ultra-small superparamagnetic iron oxide nanoparticle (SPION) with a dextran coating. Since the size exceeds the cutoff (~6 nm) for glomerular filtration, ferumoxytol is not cleared by the kidney, and instead is an excellent blood pool CA with a long intravascular half-life of about 15 h (Bremerich et al., 2007). Ferumoxytol is approved for iron-deficiency anemia but can be used in the methods disclosed herein off-label not only as a contrast agent but also as an indicator for leakage since tight junctions of the endothelial lining of the vasculature should normally prohibit exchange into the parenchymal space. BBB disruption can also facilitate exchanged of the CA into the CSF. The dynamics of ferumoxytol perfusion beyond the BBB throughout the brain upon injection can be studied and provide a dynamic measurement, or additional biomarkers. It has been found that the confinement and long residence time of ferumoxytol to the vascular space enables longitudinal and highly accurate measurements.

In some embodiments, the intravascular CA is not cleared by the kidney of the subject. In other embodiments, the intravascular CA has a size which enables kidney filtration.

In the methods described herein, ferumoxytol is administered intravenously, more specifically, as an intravenous infusion. Commercially available Feraheme® injection can be used, which is a sterile aqueous colloidal product that is formulated with mannitol. It is a black to reddish brown liquid, and is commercially available in single-dose 17 mL vials containing 510 mg of elemental iron. Each mL of the sterile colloidal solution of Feraheme® Injection contains 30 mg of elemental iron, 30 mg polyglucose sorbitol carboxymethylether, and 44 mg of mannitol. The formulation is isotonic with an osmolality of 270-330 mOsm/kg. The product contains no preservatives, and has a pH of 6 to 8.

In some embodiments, ferumoxytol is administered in a dose to produce a starting blood concentration of between about 20 and about 300 μg/mL Fe, between about 50 and about 200 μg/mL Fe, between about 50 and about 150 μg/mL Fe, between about 50 and about 100 μg/mL Fe, between about 75 and about 125 μg/mL Fe, at about 200 μg/mL Fe, or about 100 μg/mL Fe.

In some embodiments, ferumoxytol is administered at a dose of about 220 mg to about 1020 mg elemental iron, of about 255 mg to about 510 mg elemental iron, of about 510 mg to about 1020 mg elemental iron, of about 400 mg to about 600 mg elemental iron, or of about 510 mg elemental iron.

In some embodiments, ferumoxytol is administered at a dose of about 1 mgFe/kg body weight to about 8 mgFe/kg body weight, about 2 mgFe/kg body weight to about 7 mgFe/kg body weight, about 2 mgFe/kg body weight to about 6 mgFe/kg body weight, about 2 mgFe/kg body weight to about 4 mgFe/kg body weight, or about 4 mgFe/kg body weight.

As used herein, "body weight" refers to the body weight of the subject.

The methods disclosed herein, include determining presence of the CA (typically, ferumoxytol) in brain parenchyma (also referred to herein as parenchymal space) or CSF within the region of interest.

It has been found that ferumoxytol leaks into the parenchymal space as a result of BBB disruption and that QUTE-CE MM allows determining the presence of ferumoxytol which accumulates in the brain parenchyma, or leaks and accumulates within the CSF.

In some embodiments, determining presence of ferumoxytol (or generally, CA) in brain parenchyma includes assigning signal acquired using QUTE-CE MM on a voxel basis to parenchymal space within the region of interest. Ferumoxytol entering the CSF can increase signal from CSF-filled compartments, including the glyphatic system. Further, determining presence of ferumoxytol (or, generally, contrast agent) in brain parenchyma can include calculating the voxel wise change of the intensity of the acquired signal from a first acquired signal at a time before ferumoxytol is present in the brain parenchyma (typically, at a time before intravascular administration of ferumoxytol) to a subsequently acquired signal after ferumoxytol administration. When signal is acquired repeatedly (e.g., continuously or periodically) from the time that ferumoxytol is administered, the methods disclosed herein also allow following the dynamics of ferumoxytol accumulation in the brain parenchyma or CSF.

Numerous clinical MRI studies using ferumoxytol have been conducted in children and adults, demonstrating no major adverse effects (Muehe et al., 2016). Accordingly, the methods disclosed herein can be readily used in the clinic.

The methods disclose herein can be used to determine BBB disruption, and accordingly, BBB integrity, in subjects in need thereof. As used herein, a "subject in need thereof", refers to (i) a subject who is being referred by a physician to have an MM to determine BBB disruption, (ii) a subject who is suspected or has been diagnosed by a physician to have a disrupted BBB, (iii) a subject who has a disrupted BBB, and (iv) a subject with elevated risk for BBB disruption because of meeting risk factors for BBB disruption (e.g., a professional athlete prone to concussions, or genetic risk factors such as one or two APOE e4 genes indicating a higher risk for Alzheimer's disease). BBB disruption can be characterized by hyperpermeability of endothelial walls, damage to basement membranes, and enlargement of surrounding perivascular space allowing protein, macrophage, and lymphocyte invasion and $\beta$-amyloid (A$\beta$) deposition (Held et al., 2017).

In embodiments, the subject in need thereof is a subject who has or had a traumatic brain injury, has had or has a stroke, has type 2 diabetes, or has a central nervous system (CNS) disorder, for example, amyotrophic lateral sclerosis, frontotemporal dementia, Huntington's disease, Alzheimer's disease or related dementia, Parkinson's disease, and mental illnesses, such as schizophrenia and depression.

QUTE-CE MRI is can allow the diagnosis of early capillary dysfunction in subjects prior to, or during early stage CNS disorders.

In embodiments, the subject in need thereof is a subject who has a minor cognitive impairment.

In embodiments, the subject in need thereof is a subject who has an early stage CNS disorder. Examples of early stage CNS disorders include, but are not limited to, early stage amyotrophic lateral sclerosis, early stage Huntington's disease, early stage Alzheimer's disease or related dementia, early stage Parkinson's disease, early stage frontotemporal dementia, or an early stage minor cognitive impairment.

As used herein, "subject" refers to a mammal, including, but not limited to, a human or non-human mammal, such as a bovine, equine, canine, ovine, rodent, or feline.

Disease models in small animals, including transgenic models of multiple CNS disorders, such as Huntington's Disease, Alzheimer's disease and Parkinson's disease, can also be quantified with the technology.

The Alzheimer's Association study published a study on the economic benefit early AD detection. The model included the entire U.S. population in 2018, with early detection measures beginning in 2020. Differences in expected costs come from two primary sources: "1) there is a 'spike' in costs during the period immediately before and after diagnosis, and this spike is smaller when diagnosis is made during the MCI stage, and 2) medical and long-term care costs are lower in people with diagnosed and managed MCI and dementia than in people with unmanaged MCI and dementia."

With 80M people in the age range of 45-64, a 1% diagnostic check per year from this population would yield 800K scans, with a total gross cost of $1.6B-$2.8B. If all AD cases with mixed vascular pathology are diagnosed early the cost benefits for the current US population would be as much as $3.16 trillion (calculated as 40% of the potential $7.9 trillion in savings for all AD), or simply $12.72-$92.56 billion per year from 2025-2050 (see Graph); specifically, these cost savings would be to Medicare (47%), Medicaid (32%) and other insurers (20%). Based on the potential financial benefits to insurers, we project that insurance companies will cover the costs of these early diagnostic tests. With insurance companies willing to pay and 80M people standing to benefit, we expect health facilities and MRI manufacturers to integrate and use the technology.

QUTE-CE MRI can be used for identifying hyper- or hypo-vascularization, small vessel density, BBB permeability and vascular reserve and vascular responsivity to $CO_2$ challenge at the individual voxel and regional levels using a 3D MM atlas of the brain (e.g. a human atlas for human subjects). Quantitative vascular mapping of the rat brain CBV starts with acquisition of pre- and post-ferumoxytol scans. A 3D UTE sequence with optimized parameters for vascular contrast and quantification are utilized. Field corrections for coil sensitivity (B1−) and flip-angle distribution (B1+) are applied along with motion correction between the pre- and post-contrast images. A voxel-wise calculation for the quantitative CBV (qCBV) is performed to produce the qCBV maps after using a two-volume blood/tissue model with knowledge of blood intensity obtained from a large vessel. For the rat models described here, voxels are distributed into an anatomically segmented atlas with 173 regions for quantitative analysis of the whole brain. Statistically significant abnormalities are found by comparing healthy rats to those of the relevant disease model or indication.

For identifying regions of BBB disruption, the regional CBV would apparently be increasing over time due to increase signal from CA leakage into the brain parenchyma or CSF.

In some embodiments, the quantitative signal intensity can be used to determine BBB disruption if the slope of intensity vs. time curve is positive, or not decreasing according to CA clearance from the vascular compartment through the liver or the kidney.

Further Definitions

As used herein, the singular forms "a," "an" and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

EXAMPLES

The present examples are non-limiting implementations of the present technology.

Example 1. Early Detection of Cerebral Microbleeds Following Mild Traumatic Brain Injury Using QUTE-CE MRI Quantitative ultra-short time-to-echo contrast-enhanced (QUTE-CE) MRI with superparamagnetic iron oxide nanoparticle (SPION) ferumoxytol was used to identify CA accumulation in brain parenchyma due to BBB leakage, including or not including blood, to detect microbleeds in mild traumatic brain injury (mTBI) animals.

Materials and Methods

Procedure: Sprague Dawley rats were divided into two groups: control group and TBI group which received 3 mild hits for 3 continuous days. Rats in TBI group underwent QUTE-CE MRI before and immediately after ferumoxytol administration (for a 200 µg/ml iron concentration in the blood) for 1.5 hours while control group underwent the same imaging sessions without TBI. Quantitative global percentage of signal intensity change map based on baseline as determined by statistical significance of a positive slope and regional percentage of signal intensity over time were calculated from QUTE-CE MRI using a 174-region rat brain atlas to examine regions of interest.

TBI: The pneumatic pressure drive, 50 g compactor described by Viano et. al. was replicated (see FIG. 1) and reproduced consistently the 7.4, 9.3 and 11.2 m/s impact velocities described for mild, medium and severe rat head injury, respectively. The data reported provided in this example all came from the 7 m/s impact velocities as determined using high-speed video recordings. Rats were impacted once, twice, and three times with a one-day interval between each impact.

QUTE-CE MRI: A Bruker Biospec 7.0 T/20 cm USR horizontal magnet (Bruker, Billerica, Mass., USA) was used. The following parameters were used in the QUTE-CE MM: TE: 13 µs; TR: 4 ms; FA: 20°; FOV: 3 cm by 3 cm by 3 cm; Matrix Size: 180 by 180 by 180; and Resolution: 167 µm by 167 µm by 167 µm.

Results

Figure 3:
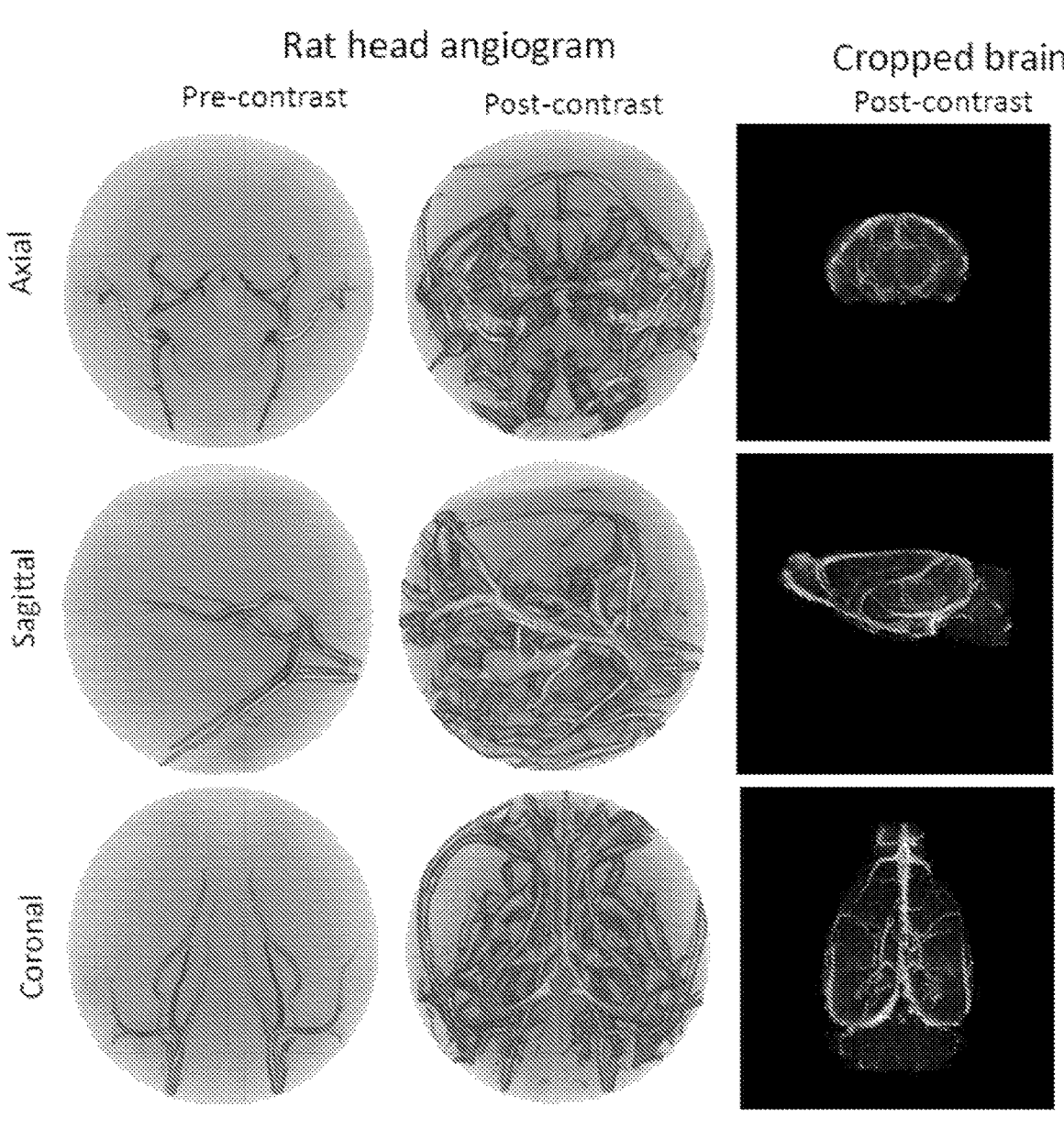
FIG. 3 provides rat head angiograms obtained using QUTE-CE MRI.
Figure 4A:
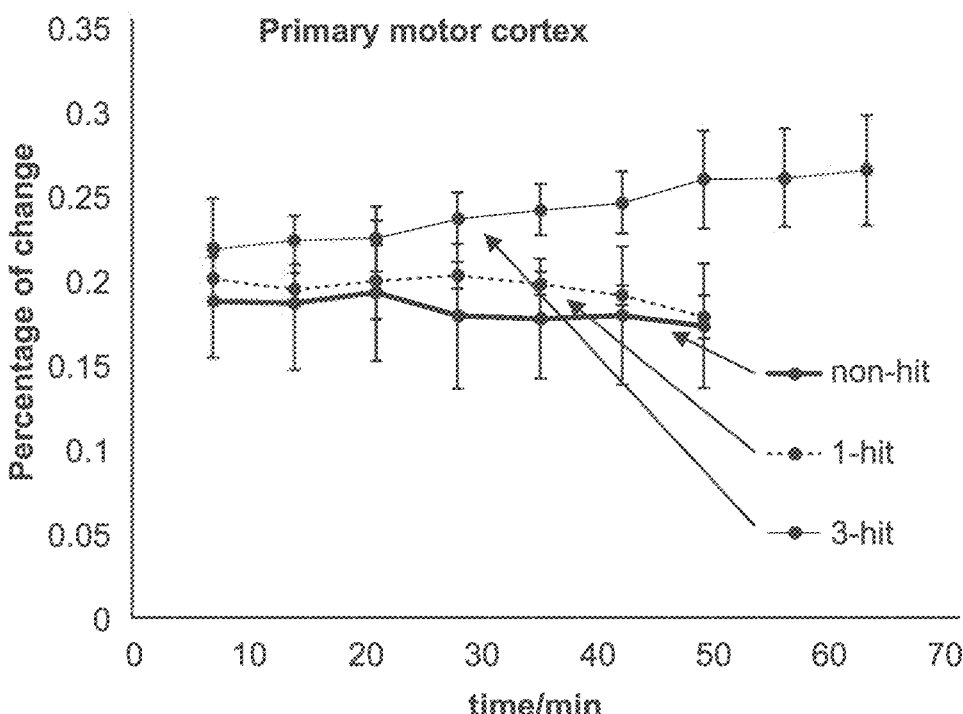
FIG. 4A provides a graph of the percentage of change of the quantitative signal intensity over time for the non-hit, 1-hit, and 3-hit conditions in rat for the primary motor cortex.
Figure 4B:
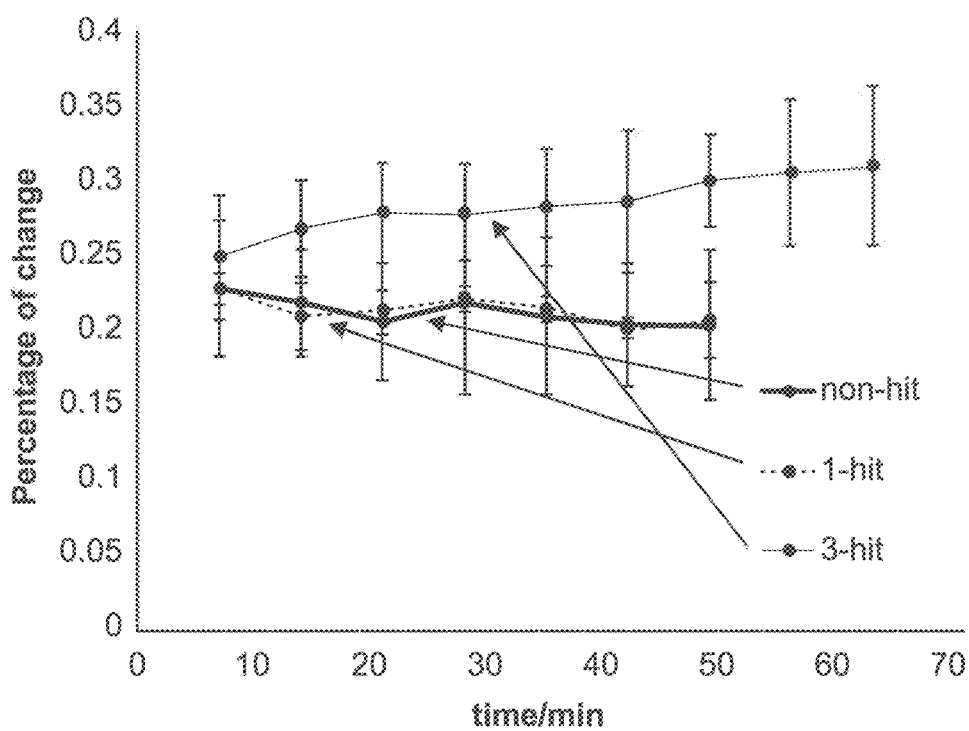
FIG. 4B provides a graph of the percentage of change of the quantitative signal intensity over time for the non-hit, 1-hit, and 3-hit conditions in rat for the secondary motor cortex.
Figure 4C:
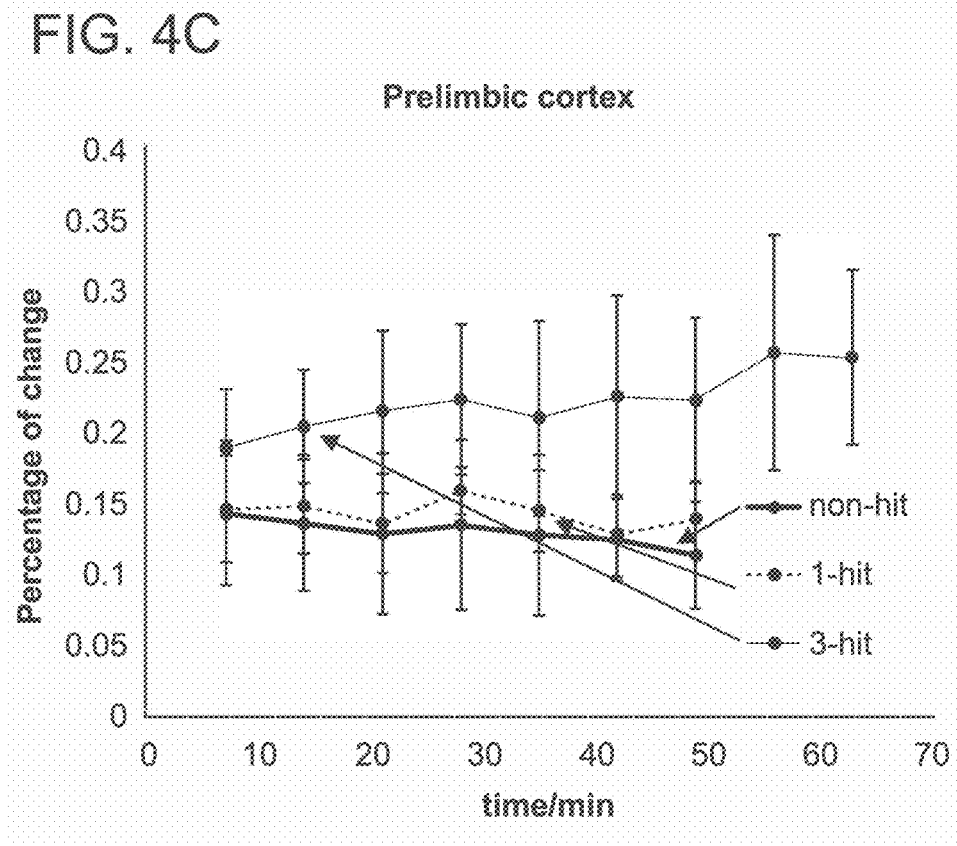
FIG. 4C provides a graph of the percentage of change of the quantitative signal intensity over time for the non-hit, 1-hit, and 3-hit conditions in rat for the prelimbic cortex.
Figure 4D:
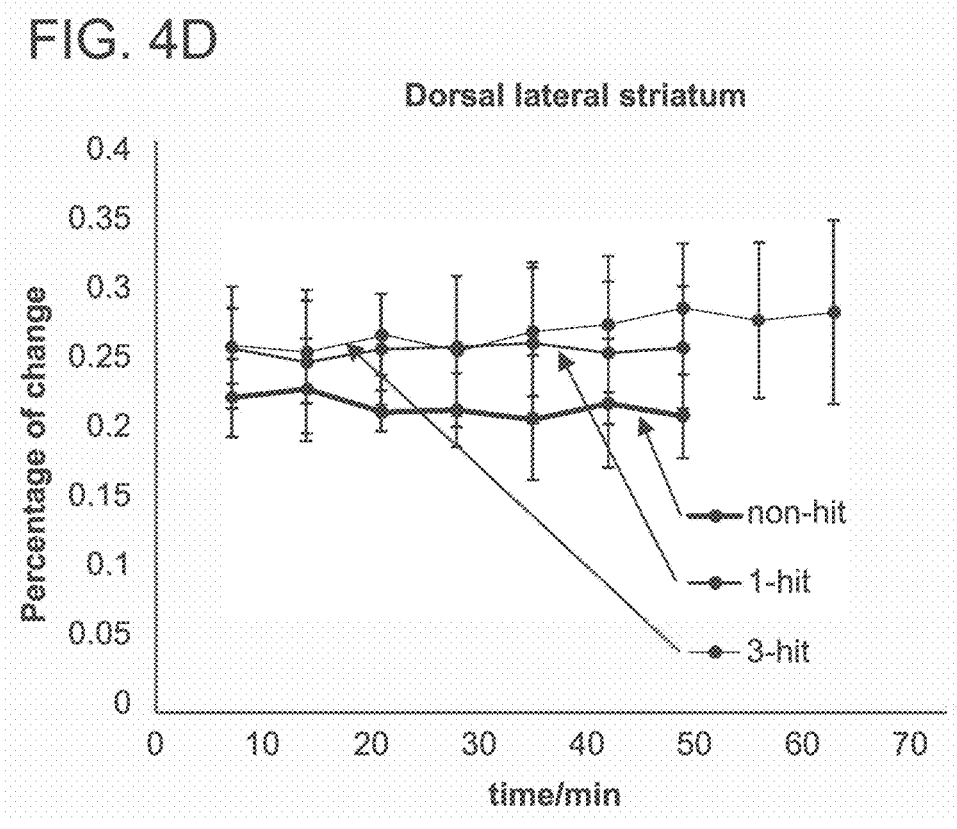
FIG. 4D provides a graph of the percentage of change of the quantitative signal intensity over time for the non-hit, 1-hit, and 3-hit conditions in rat for the dorsal lateral striatum.
Figure 4E:
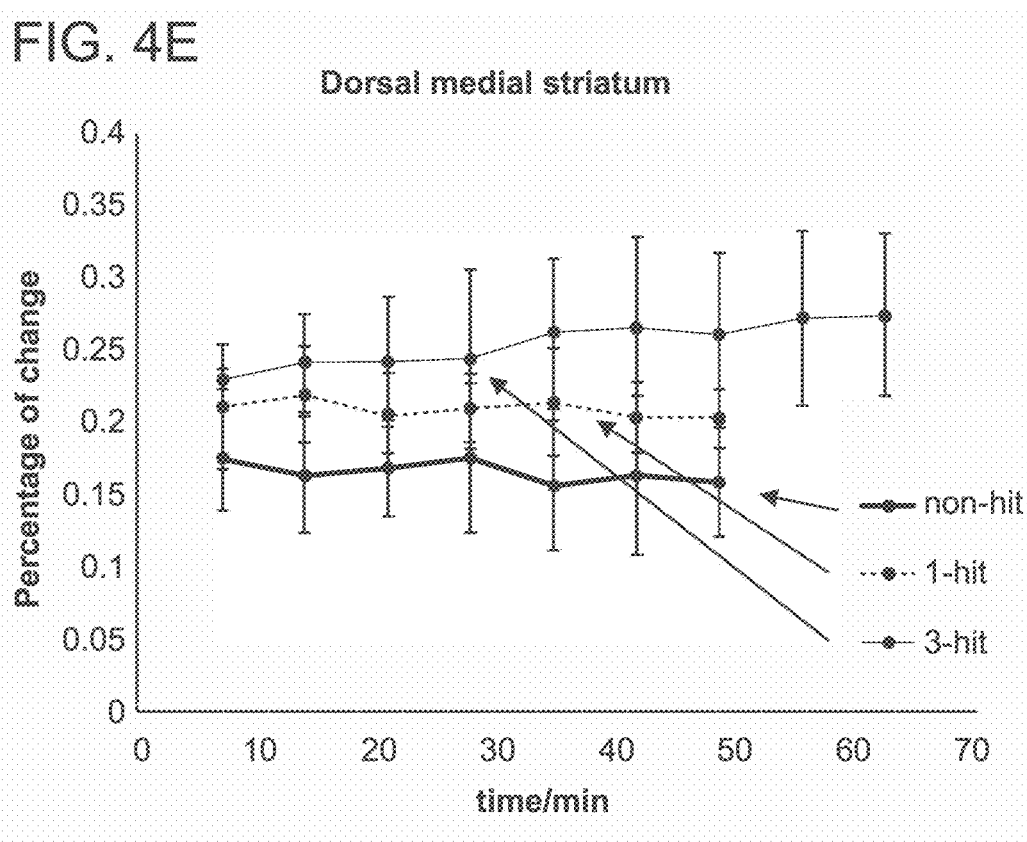
FIG. 4E provides a graph of the percentage of change of the quantitative signal intensity over time for the non-hit, 1-hit, and 3-hit conditions in rat for the dorsal medial striatum.
Figure 4F:
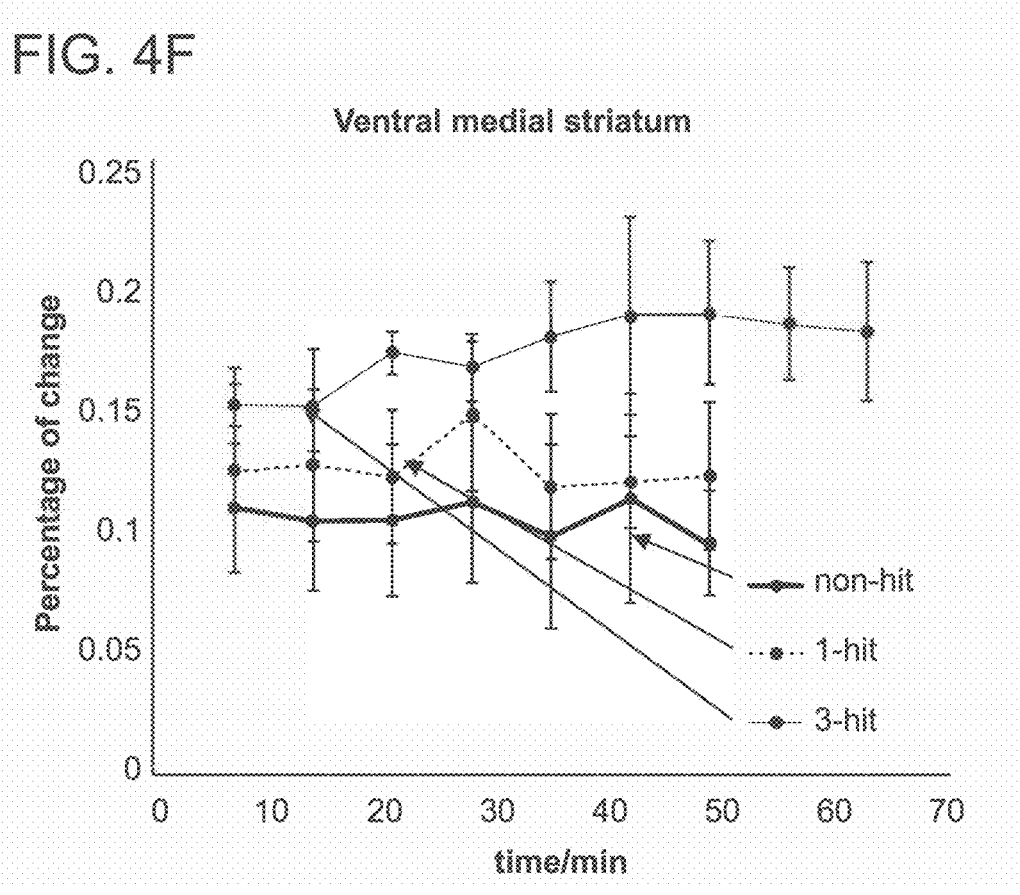
FIG. 4F provides a graph of the percentage of change of the quantitative signal intensity over time for the non-hit, 1-hit, and 3-hit conditions in rat for the ventral medial striatum.

FIG. 3 provides rat head angiograms obtained using QUTE-CE MM. The left column provides angiograms obtained pre-contrast, the middle column provides angiograms post-contrast, and the right column shows cropped brain images post-contrast. QUTE-CE MM has been shown to clearly delineate rat brain vasculature.

FIGS. 4A-4F provide graphs of the percentage of change of quantitative signal intensity over time for the non-hit, 1-hit, and 3-hit conditions in rat for the primary motor cortex, the secondary motor cortex, the prelimbic cortex, the dorsal lateral striatum, the dorsal medial striatum, and the ventral medial striatum, respectively. QUTE-CE MM has been shown to detect microbleeds following mTBI.

Figure 5A:
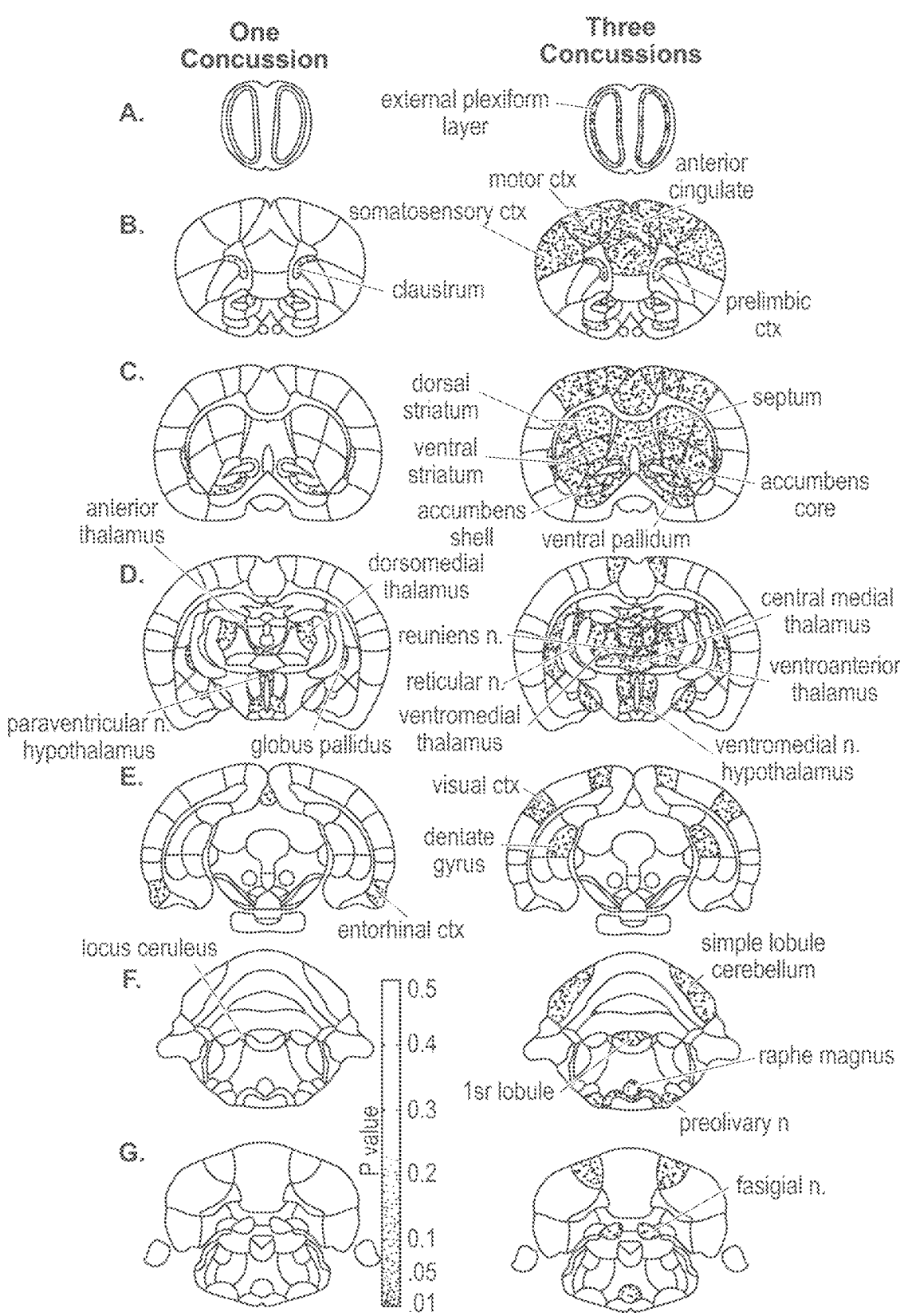
FIG. 5A provides 2D images of brain areas (shades of gray for level of significance) with putative increases in BBB permeability following one (left side) and three (right side) head injuries as compared to non-concussed controls.
Figure 5B:
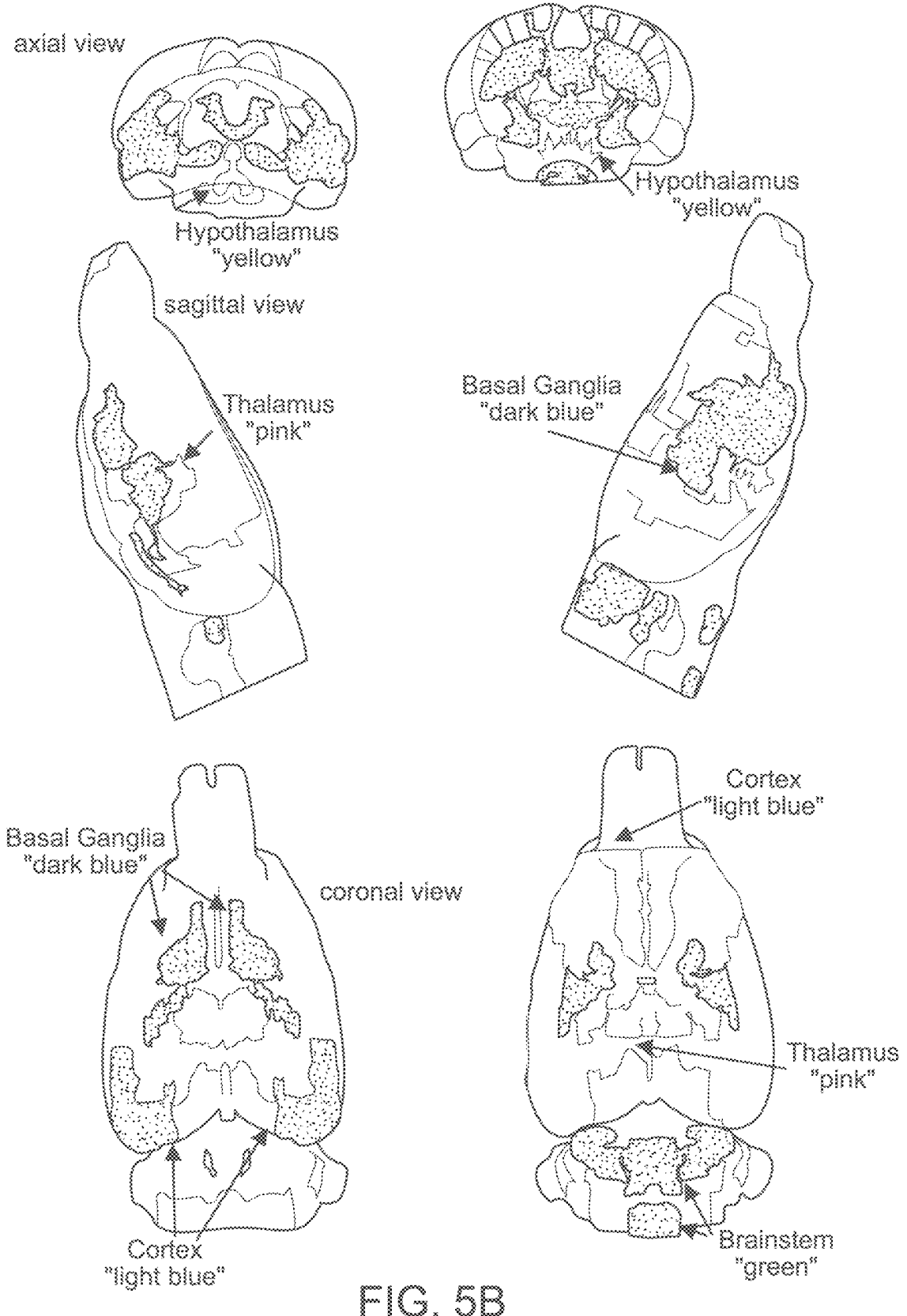
FIG. 5B shows the location and regional organization of the affected brain areas shown in FIG. 5A as 3D glass brain images.

FIG. 5A provides probability maps (indicating p value by degree of shading) showing significant increases in ferumoxytol contrast in various rat brain regions following repetitive mild head injury, one concussion/hit in the left column of probability maps and three concussions/hits in the right column of probability maps. FIG. 5B shows the location and regional organization of the affected brain areas shown in FIG. 5A as 3D glass brain images.

Rats which underwent 1 mild hit showed moderate significant BBB disruption as measured with QUTE-CE MM using ferumoxytol accumulation, indicating BBB was slightly disrupted after 1 mild concussion. Rats which underwent 3 hits showed much more significant differences in QUTE-CE MM measures of ferumoxytol accumulation in extravascular space. These differences were primarily in the cortex, hypothalamus, basal ganglia, cerebellum and brainstem. Ferumoxytol has been found to continue to leak out from the vasculature and to accumulate in brain tissues after mTBI. It has been shown that QUTE-CE MM can be used to detect microbleeds early following mTBI.

Example 2. Quantitative Imaging of Increased Blood Brain Barrier Permeability Following Single and Repetitive Mild Traumatic Brain Injury Introduction Cerebral small vessel disease (cSVD) references pathophysiological processes affecting arterioles, capillaries and venules (Pantoni, 2010). Cerebral SVD is a leading cause of dementia and thought to be a significant source of neurological disability in aging and a key pathogenic factor in Alzheimer's disease (AD) (Wardlaw et al., 2013). There is ever growing evidence that failure in the blood brain barrier (BBB) lies at the foundation of cSVD as first described by Wardlaw (Wardlaw, 2010). BBB failure is characterized by hyperpermeability of endothelial walls, damage to basement membranes, and enlargement of surrounding perivascular space allowing protein, macrophage, and lymphocyte invasion and β-amyloid (Aβ) deposition (Held et al., 2017).

Disruption in the BBB commonly occurs with traumatic brain injury (TBI) (Shlosberg et al., 2010). Mild TBI produces minimal neuropathology (Menon et al., 2010), is estimated to account for 70-90% of all TBI cases (Gardner and Yaffe, 2015) and any cognitive or behavioral deficits usually resolve within weeks of the head injury (Iverson, 2005). However, repetitive mild TBI (rmTBI) is associated with more severe and protracted cognitive, motor, and behavioral complications that may last for months and even years (De Beaumont et al., 2012). Even after the remission of symptoms, there is accumulating evidence of persistent brain injuries (Palacios et al., 2017; Rajesh et al., 2017) that carry an increased risk of dementia, Alzheimer's disease, chronic traumatic encephalopathy, and Parkinson's disease later in life (Plassman et al., 2000; Jafari et al., 2013; McKee et al., 2016).

There are multiple imaging protocols e.g., T2 Fluid Attenuated Inversion Recovery (FLAIR), Susceptibility Weighted Imaging (SWI), Diffusion-Weighted Imaging (DWI), for detecting the gross lesions that result from the neuropathological consequences of cSVD; however, they cannot quantitatively assess BBB integrity (Wardlaw et al., 2013). However, BBB leakage can be assessed with dynamic contrast enhanced (DCE) MRI (Heye et al., 2014). Indeed, DCE-MRI is the imaging technique being developed in the clinic for assessing BBB permeability changes in cSVD (Thrippleton et al., 2019). However, DCE-MRI has several limitations. The concentration versus time curve for gadolinium-based contrast agent is typically 15-30% inaccurate; therefore, DCE-MRI has not proven useful clinically (Walker-Samuel et al., 2007; Schabel and Parker, 2008). It is also difficult to model the effects of contrast agent on both T2* and T1 given the short acquisition time, and strong dependence on microstructural properties such as vessel size, tortuosity and orientation. These and other methodological issues with the use of DCE-MRI for BBB permeability have resulted in significant differences in the reported rates of leakage (Raja et al., 2018). Therefore, there exists a compelling need to develop a quantitative non-invasive method for mapping BBB integrity following rmTBI. To address this issue, a novel imaging modality, quantitative ultrashort time-to-echo, contrast enhanced (QUTE-CE) MRI (Gharagouzloo et al., 2015) was used to study changes in blood brain permeability following a single and three mild head injuries.

Materials and Methods

Animals

Subjects were all adult male Sprague Dawley rats (n=28), approximately 100 days of age and purchased from Charles River Laboratories (Wilmington, Mass., USA). Animals were housed in Plexiglas cages (two per cage) and maintained in ambient temperature (22-24° C.) on a 12:12 light-dark cycle (lights on at 07:00 a.m.). Food and water were provided ad libitum. All methods and procedures described were approved by the Northeastern University Institutional Animal Care and Use Committee (IACUC). The Northeastern facility is AAALAC accredited with OLAW Assurance and is registered with the USDA. All housing, care, and use followed the Guide for the Care and Use of Laboratory Animals (8th Addition) and the Animal Welfare Act.

Rats were subjected to three continuous mild head injuries with 24 hours apart as previously described (Kulkarni et al., 2019). All rats went through MRI scans 24 hours before the first head injury (non-hit, n=9), right after the first head injury (1-hit, n=9) and right after the third head injury (3-hit, n=7). A catheter containing heparinized saline was inserted into tail vein before MRI scans. An anatomical MRI and one QUTE-CE MRI were taken prior to an i.v. bolus of 10 mg/ml Fe of ferumoxytol. The injected volume was tailored for each rat (assuming 7% blood by body weight) to produce a starting blood concentration of 200 µg/ml Fe (twice the clinical dose approved for use in humans). 7 continuous QUTE-CE MM scans were taken immediately after ferumoxytol administration. In a separate study using the protocol above, nine rats, three per group were studied for extravasation of labelled dextran to validate BBB permeability.

Momentum Exchange Model

Concussion were generated with a pneumatic pressure drive, 50 g compactor described by Viano and colleagues (Viano et al., 2009) and refined by Mychasiuk et al (Mychasiuk et al., 2016) to reliably produced the 7.4, 9.3, and 11.2 m/s impact velocities described for mild, medium and severe rat head injury, respectively. We have used this model to publish on the neuroradiological effects of rmTBI in rats (Kulkarni et al., 2019). The data reported here all came from the 7.4 m/s impact velocities. The impact piston was directed to the top of the skull, midline, in the approximate area of Bregma. All control and TBI rats were anesthetized with 2% isoflurane. Rats were awake and ambulatory within 5-7 min after anesthesia and concussion.

Imaging

Studies were done on a Bruker Biospec 7.0T/20-cm USR horizontal magnet (Bruker, Billerica, Mass., USA) and a 20-G/cm magnetic field gradient insert (ID=12 cm) capable of a 120 µs rise time. Radio frequency signals were sent and received with a quadrature volume coil built into the rat restrainer (Animal Imaging Research, Holden, Mass., US). All rats imaged under 1-2% isoflurane while keeping a respiratory rate of 40-50 breadths/min.

At the beginning of each imaging session, a high-resolution anatomical data set was collected using the RARE pulse sequence with following parameters, 35 slice of 0.7 mm thickness; field of view [FOV] 3 cm; 256×256; repetition time [TR] 3900 msec; effective echo time [TE] 48 msec; NEX 3; 6 min 14 sec acquisition time.

The QUTE-CE MRI image parameters are: TE=13 µs, TR=4 ms, FA=15°, RF pulse bandwidth of 200 kHz. A 3×3×3 cm3 field-of-view was used with a matrix size of 180×180×180 to produce 167 µm isotropic resolution.

Image Processing

Images were motion-corrected, aligned spatially, and resliced using MATLAB SPM12 toolbox developed at UCL. The pre-contrast QUTE-CE images were set as the baseline. For each rat in each imaging session, the voxel wise percentage change of signal intensity for each scan time point (post-con) was calculated as (post-con−baseline)/baseline*100%. The T2-weighted RARE anatomical data for each rat taken at each imaging session was fit to a 3D MM Rat Brain Atlas © (Ekam Solutions LLC, Boston, Mass., US) with 173 segmented annotated brain areas using software developed at Northeastern University Center for Translational Neuroimaging (CTNI). The fitted atlas was transferred to UTE imaging.

Once the images were co-registered to the atlas, custom MATLAB code was used to mask individual brain regions for ferumoxytol measurement. We previously demonstrated that B1-corrected QUTE-CE MM signal intensity could be used to generate voxel-based CBV maps of 500,000 voxels distributed into 173 brain areas using this method (Gharagouzloo et al., 2017).

Data Analysis and Statistics

QUTE-CE time-variant curves were compared by two-way ANOVA with Tukey's post hoc test for simple effect comparison at each time point. Parameters extracted from fitting curves were compared using student's t-test. Mode of percentage change distribution for each of the 173 brain areas for control one and three hit rats was statistically compared using a Wilcoxon rank-sum test with the alpha set at 0.05.

Histological Analysis

Changes in BBB permeability after rmTBI was confirmed via injection of FITC-fluorescent dextran, as previously described (Natarajan et al., 2017). 70 kDa FITC-dextran was injected intravenously to rats immediately after QUTE-CE imaging as noted above. One hour after injection, rats were perfused and their brains collected, post fixed in 4% PFA for 24 hours, cryopreserved in 30% sucrose for 48 hours, and subsequently sectioned in 40-micron increments. Sections were stained with *Lycopersicon esculentum* (Tomato) lectin to label the vasculature and imaged using a laser scanning confocal microscope. Increased FITC signal in the perivascular space was indicative of increased BBB permeability. Permeability was quantified by analyzing the total area of FITC-dextran above a thresholded pixel intensity to account for background noise (Natarajan et al., 2017). Data was normalized to the substantia nigra for each subject to eliminate subject bias. Images were taken using a Zeiss LSM 880 laser scanning confocal microscope in Northeastern University's Institute for Chemical Imaging of Living Systems. Regions in rmTBI subjects found with increased BBB permeability via QUTE-CE (orbital and motor cortices) were compared to areas that demonstrated no significant permeability differences (substantia nigra).

Results

Figure 6A:
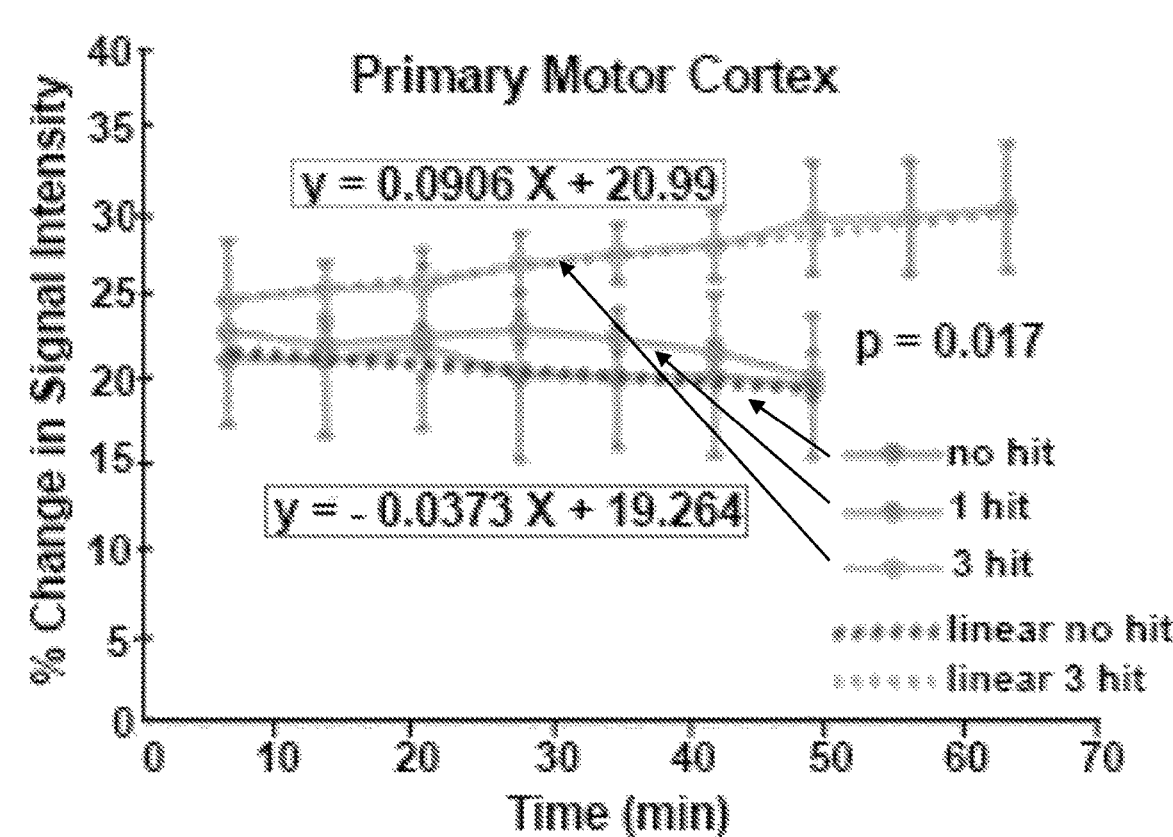
FIG. 6A provides a graph of the percentage of the change of the quantitative signal intensity for the non-hit, 1-hit, and 3-hit conditions in rat for with no hits, one hit and three hits for the primary motor cortex in rats; dashed trend lines are shown for no hit and three hits together with their linear equation.
Figure 6B:
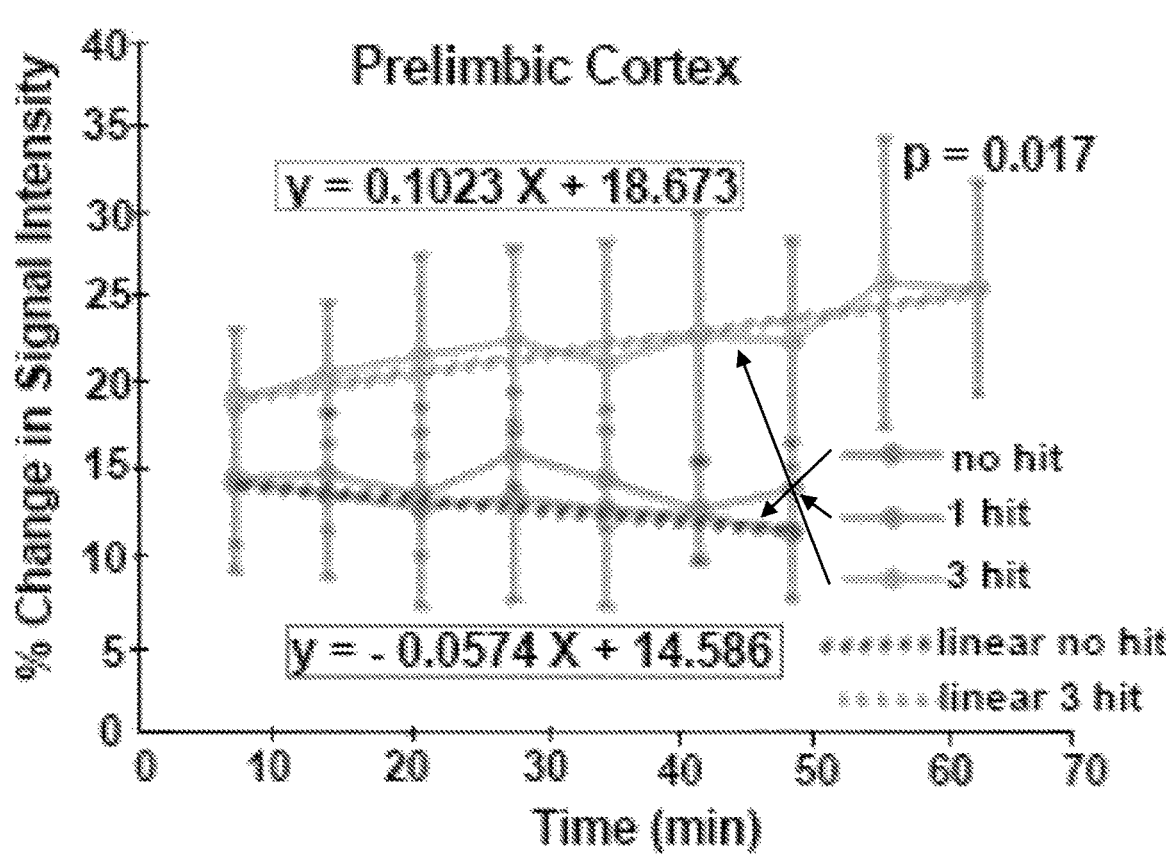
FIG. 6B provides a graph of the percentage of the change of the quantitative signal intensity for the non-hit, 1-hit, and 3-hit conditions in rat for with no hits, one hit and three hits for the prelimbic cortex in rats; dashed trend lines are shown for no hit and three hits together with their linear equation.

FIG. 6A and FIG. 6B present each an example from the forebrain cortex (primary motor cortex in FIG. 6A and prelimbic cortex in FIG. 6B) showing time-resolved measurements for changes in QUTE-CE MRI signal intensity in rats with no hits, one hit and three hits. Dashed trend lines are shown for no hit and three hits together with their linear equation. Intensity is proportional to the concentration of the contrast agent via the spoiled gradient echo (SPGR) equation (Gharagouzloo et al., 2017), and will decrease over time as the contrast agent leaves the blood (non-hit animals). In the case of leakage, the signal intensity will increase as seen in the three hit rats over the 70 min time course as the BBB is compromised in these brain areas.

Table 1 and 2 below report only brain areas with significant changes in BBB permeability following one and three hits as compared to no hits. The list for each table is ranked in order of significance and truncated from the 173 brain areas in the rat MRI atlas.

TABLE 1

| Brain Area | Pre Hit | | | 1 Hit | | |
|---|---|---|---|---|---|---|
| | AVG | SD | | AVG | SD | P-val |
| CA3 hippocampus ventral | 0.37 | 0.17 | < | 0.53 | 0.11 | 0.004 |
| claustrum | 0.1 | 0.02 | < | 0.14 | 0.03 | 0.012 |
| prelimbic ctx | 0.15 | 0.04 | < | 0.19 | 0.04 | 0.017 |
| secondary motor ctx | 0.19 | 0.07 | < | 0.27 | 0.04 | 0.041 |
| primary motor ctx | 0.18 | 0.04 | < | 0.23 | 0.03 | 0.048 |

TABLE 2

| Brain Area | Pre Hit | | | 3 Hit | | |
|---|---|---|---|---|---|---|
| | AVG | SD | | AVG | SD | P-val |
| lateral orbital ctx | 0.06 | 0.07 | < | 0.11 | 0.05 | 0.002 |
| claustrum | 0.10 | 0.02 | < | 0.16 | 0.04 | 0.007 |
| secondary motor ctx | 0.19 | 0.07 | < | 0.31 | 0.06 | 0.009 |
| ventral pallidum | 0.16 | 0.05 | < | 0.23 | 0.06 | 0.009 |
| primary somatosensory ctx jaw | 0.17 | 0.04 | < | 0.23 | 0.04 | 0.010 |
| primary somatosensory ctx shoulder | 0.23 | 0.06 | < | 0.27 | 0.06 | 0.012 |
| endopiriform nucleus | 0.10 | 0.05 | < | 0.15 | 0.07 | 0.013 |
| primary motor ctx | 0.18 | 0.04 | < | 0.26 | 0.05 | 0.014 |
| medical preoptic area | 0.11 | 0.06 | < | 0.16 | 0.08 | 0.015 |
| anterior cingulate ctx | 0.26 | 0.04 | < | 0.35 | 0.06 | 0.015 |
| CA3 hippocampus ventral | 0.37 | 0.17 | < | 0.49 | 0.15 | 0.018 |
| ventral medial striatum | 0.12 | 0.03 | < | 0.18 | 0.05 | 0.023 |
| ventral lateral striatum | 0.17 | 0.05 | < | 0.23 | 0.04 | 0.024 |
| accumbens shell | 0.11 | 0.03 | < | 0.17 | 0.07 | 0.025 |
| dorsal lateral striatum | 0.21 | 0.05 | < | 0.27 | 0.05 | 0.026 |
| medial orbital ctx | 0.02 | 0.23 | < | 0.36 | 0.26 | 0.029 |
| primary somatosensory ctx trunk | 0.22 | 0.06 | < | 0.27 | 0.05 | 0.036 |
| prelimbic ctx | 0.15 | 0.04 | < | 0.22 | 0.06 | 0.038 |
| arcuate nucleus | 0.19 | 0.12 | < | 0.33 | 0.19 | 0.041 |
| accumbens core | 0.09 | 0.03 | < | 0.14 | 0.04 | 0.042 |
| lateral amygdala | 0.35 | 0.20 | < | 0.45 | 0.11 | 0.047 |
| anterior amygdala | 0.06 | 0.07 | < | 0.14 | 0.13 | 0.049 |
| lateral septum | 0.21 | 0.06 | < | 0.28 | 0.06 | 0.049 |
| medial septum | 0.15 | 0.04 | < | 0.26 | 0.10 | 0.049 |

Figure 7:
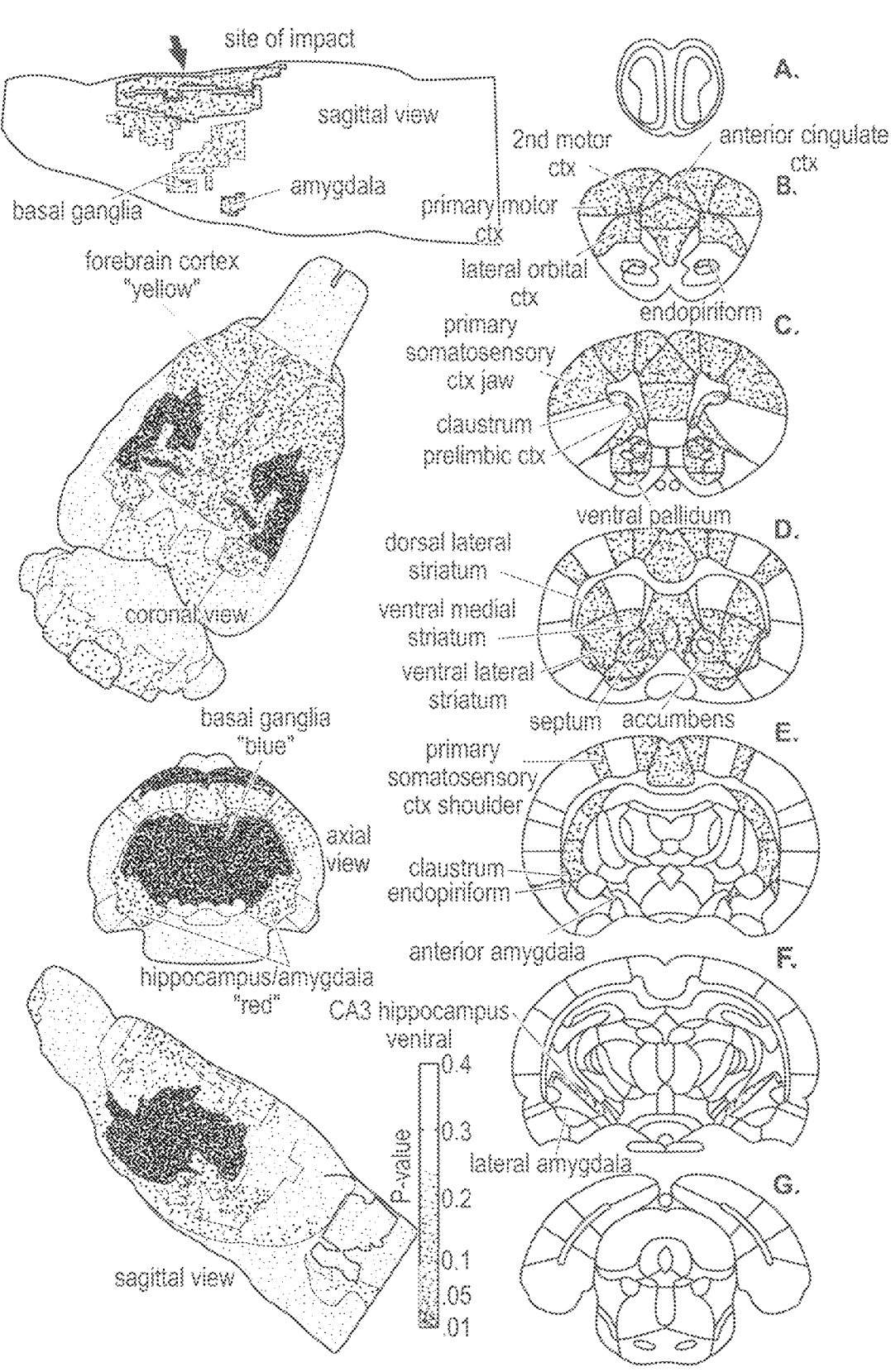
FIG. 7 provides 2D images of brain areas (shades of gray for level of significance) with putative increases in BBB permeability following one and three head injuries as compared to non-concussed controls; areas most affected were in the forebrain (sections B and C) but did extend caudally to include the cerebellum and deep cerebellar n (sections F and G).

In all cases BBB permeability is increased as compared to rats with no hits. Rats with a single hit present with only five brain areas with increased permeability: ventral CA3 hippocampus, claustrum, prelimbic, secondary and primary motor cortices. These same brain areas are represented in Table 2 in the three hit rats together with 19 other areas in the forebrain. The location of these brain areas can be visualized in the 2D axial, probability heat maps (A-G) in FIG. 7. The site of impact (arrow) is shown in the sagittal section in the upper left corner. The location and regional organization of these affected brain areas are summarized in the 3D glass brains showing the forebrain cortex, basal ganglia and hippocampus/amygdala. The cortical areas nearest the site of impact (e.g. anterior cingulate, secondary and primary motor cortices, lateral orbital and somatosensory cortices) are highly significant for increased BBB permeability as would be expected. Interestingly the basal ganglia (e.g. section D, dorsal lateral/ventral lateral/ventral medial striatum, accumbens core and shell, ventral pallidum, medial and lateral septum) are areas distal to the site of impact but vulnerable to rmTBI as are the ventrally located CA3 hippocampus and anterior and lateral amygdala.

Figure 8:
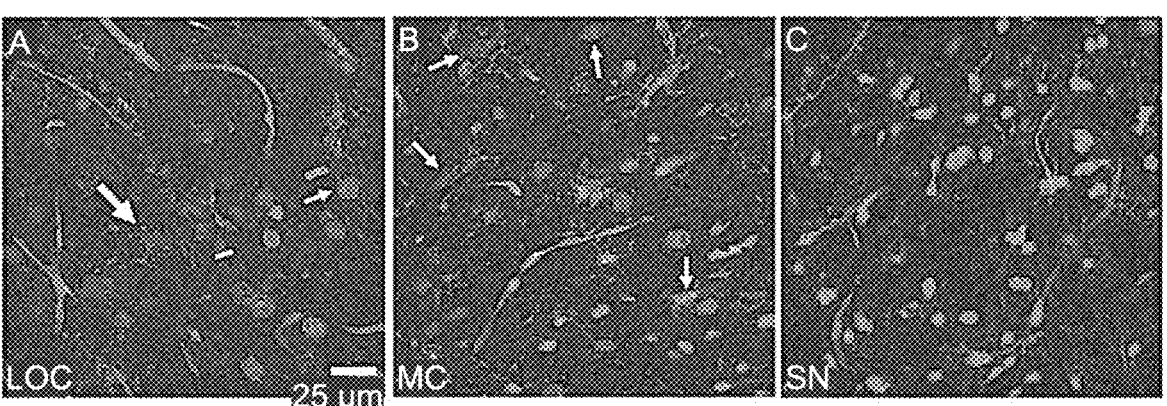
FIG. 8 provides images of fluorescent staining of vasculature via Tomato lectin which demonstrates increases in FITC-dextran accumulation within the parenchyma and vascular cells of the (A) lateral orbital (LOC) and (B) 2nd motor (MC) cortices, but not the (C) substantia nigra (SN). Quantification of permeability in the (D) LOC and (E) MC.
Figure 8:
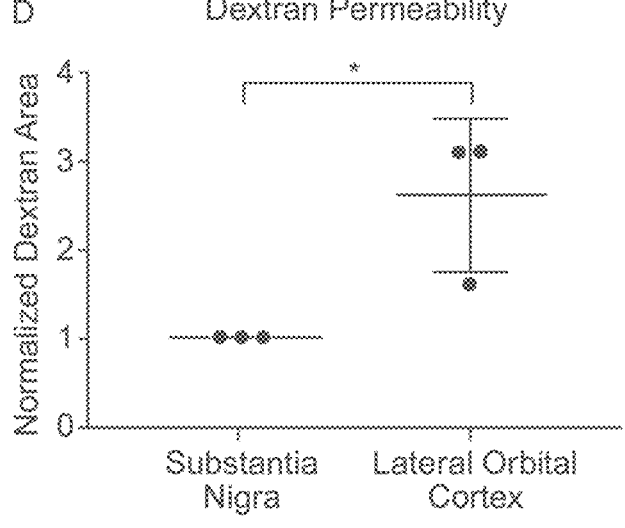
Figure 8:
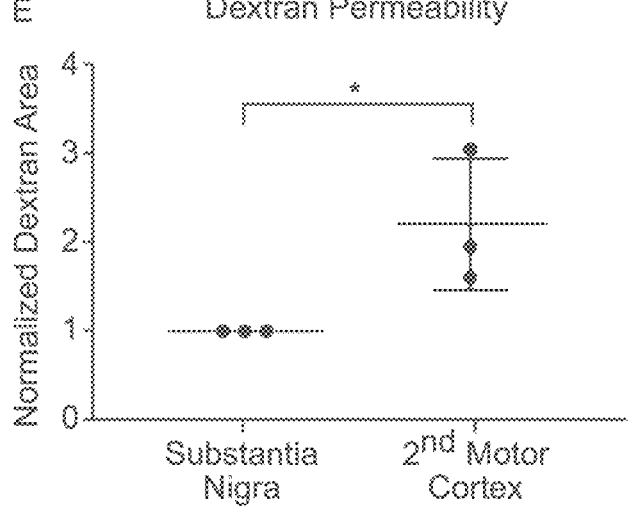
Figure 9A:
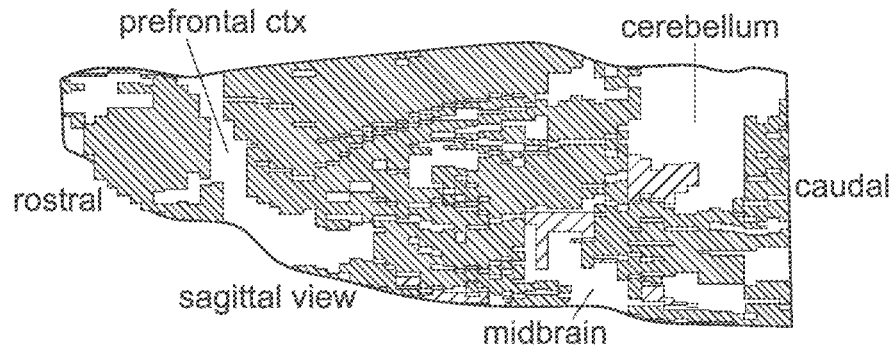
FIG. 9A provides images of rat brain regions with regions gray shaded which showed significantly greater BBB permeability in type 2 diabetic, BBZDR/Wor rats as compared to wild-type controls; areas in white localized to the prefrontal ctx, midbrain and cerebellum were not significantly different.
Figure 9A:
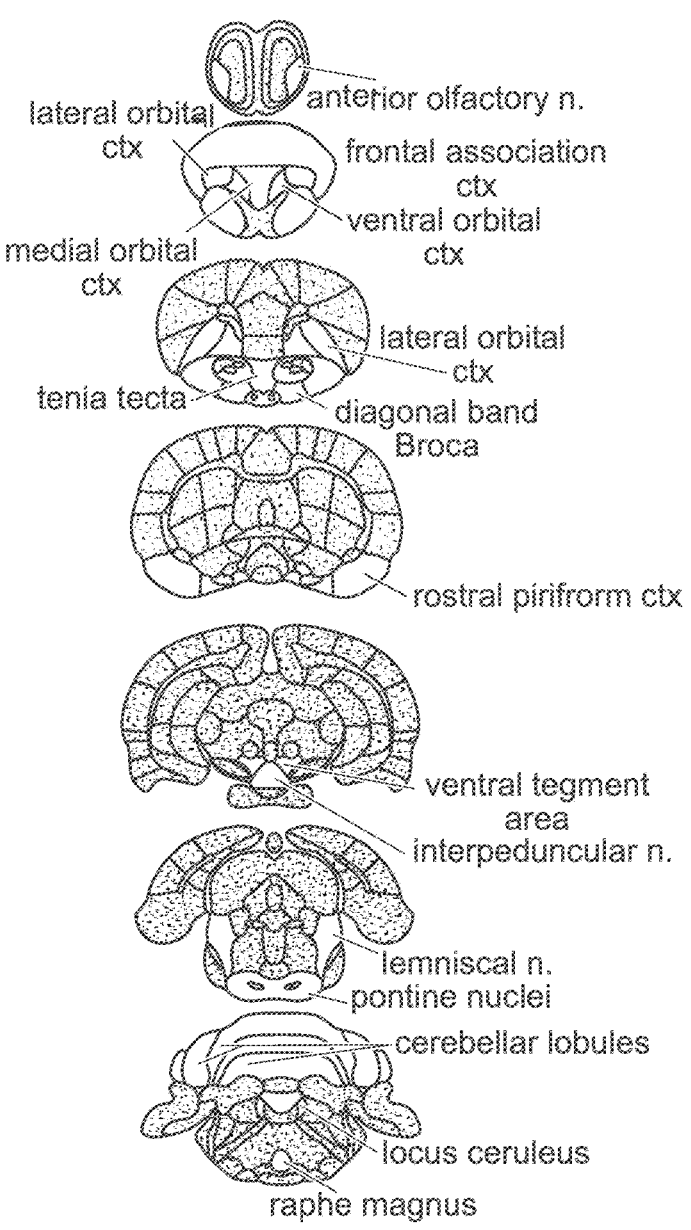
Figure 9B:
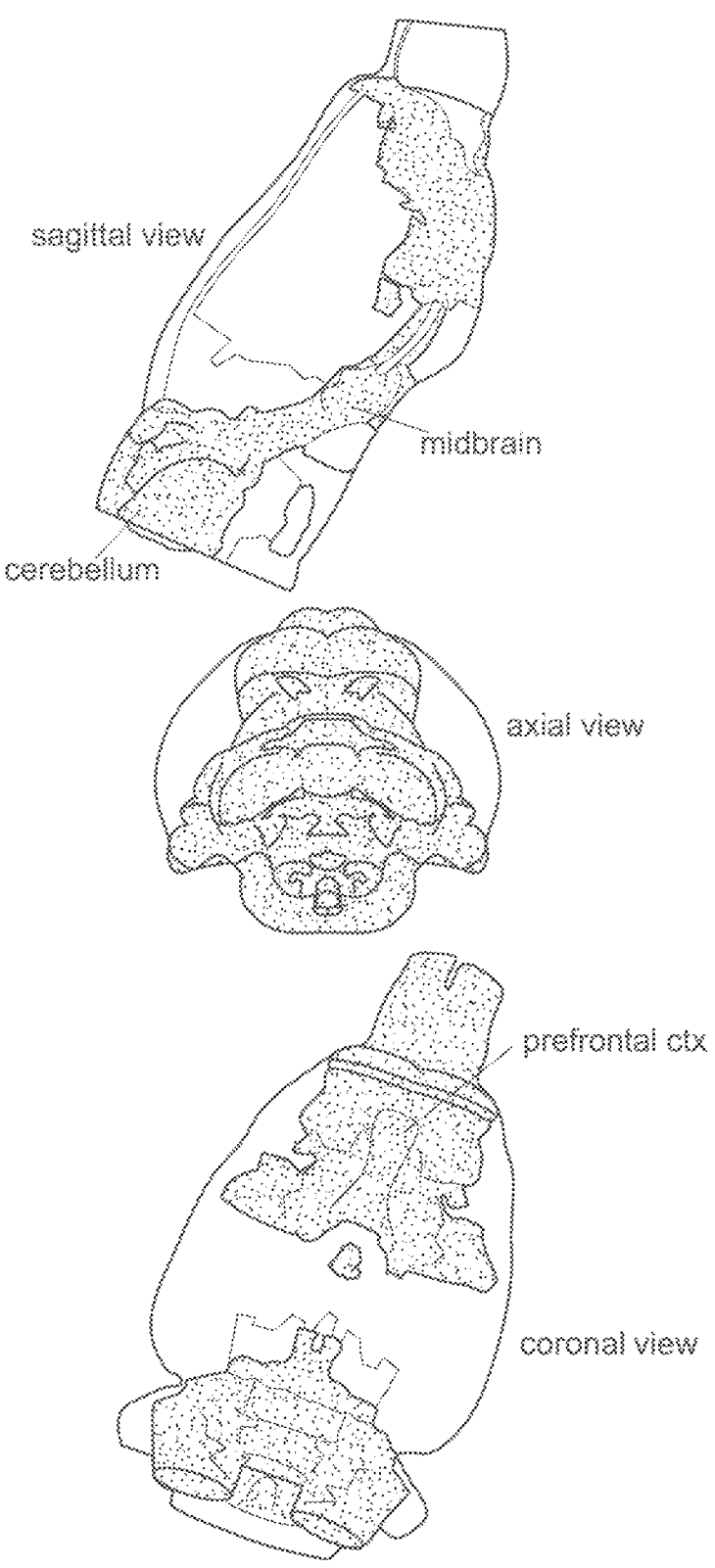
FIG. 9B provides glass brain images in which the areas in white of FIG. 6A are coalesced into 3D volumes.

Brain regions with increased permeability as identified by QUTE-CE were validated via FITC-dextran injection (FIG. 8). Fluorescent imaging and quantitative image analysis demonstrated that rmTBI leads to an increase in BBB permeability in both the second motor and orbital cortex (a, b, d) (FIG. 8). This is highlighted by increased dextran accumulation in the brain parenchyma (white arrows) as well as within vascular cells, potentially suggesting increased retention by endothelial cells. In contrast, low levels of parenchymal and vascular dextran were observed in the substantia nigra (c, d) (FIG. 8). These results are in agreement with QUTE-CE results.

Discussion

The study was designed to evaluate the vulnerability of the BBB to a single and repetitive mild hit to the head using a novel imaging protocol QUTE-CE. Using a momentum exchange model (Kulkarni et al., 2019), we were able to deliver repetitive, mild head impacts without neuroradiological signs of contusion. This model combined with non-invasive QUTE-CE enabled us to investigate two clinically relevant questions: 1) Does a single mild hit to the head compromise BBB integrity and, 2) Do several mild hits within days of one another exacerbate the risk of BBB injury? The imaging data confirmed that a single hit, did indeed, increase BBB permeability in brain areas near the site of impact and that rmTBI broadened the area of vulnerability to brain regions distal to site of impact.

In this study, three mild hits had greater consequences on BBB permeability than a single mild hit. Not unexpectedly, rmTBI has serious consequences on brain structure and function as reported previously using the momentum exchange model showing alterations in indices of anisotropy reflecting white and gray matter damage and loss of functional connectivity between various brain regions (Kulkarni et al., 2019). There are numerous human and animal studies using various in-vivo and in-vitro methods showing rmTBI separated by short intervals of time posse a significant risk to the brain and vulnerability to neurodegenerative disorders with aging (Yoshiyama et al., 2005; Prins et al., 2013; Weil et al., 2014; Qin et al., 2018). With QUTE-CE we have included quantitative measures of increased BBB permeability as a method to non-invasively follow the consequences of mild head injury at the level of the neurovascular unit. The etiology of idopathic Alzheimer's and Parkinson's diseases is unknown although all neurodegenerative diseases are thought to be linked cSVD with aging (Wardlaw et al., 2013). Since failure in the BBB lies at the foundation of cSVD (Wardlaw, 2010), QUTE-CE offers a quantitative non-invasive method for assessing the severity of BBB injury within hrs of head injury and alerting clinicians to future risks of dementia and neurodegenerative diseases.

QUTE-CE was developed as a quantitative vascular biomarker (Gharagouzloo et al., 2015). Ferumoxytol MRI with optimized 3D Ultra-Short Time-to-echo (UTE) Pulse Sequences produces angiographic images unparalleled to time-of-flight imaging or gadolinium-based first-pass imaging. The contrast agent ferumoxytol, is an ultra-small superparamagnetic iron oxide nanoparticles (USPION) with a dextran coating. Since the size exceeds the cutoff (~6 nm) for glomerular filtration, ferumoxytol is not cleared by the kidney, and instead is an excellent blood pool contrast agent with a long intravascular half-life of ~15 h (Bremerich et al., 2007). Numerous clinical MRI studies using ferumoxytol have been conducted in children and adults, demonstrating no major adverse effects, thus QUTE-CE can be readily used in the clinic to study BBB permeability (Muehe et al., 2016).

Example 3. Evaluating Blood-Brain Barrier Permeability in a Rat Model of Type 2 Diabetes Quantitative ultrashort time-to-echo, contrast enhanced (QUTE-CE) MM (Gharagouzloo et al., 2015) was used to study changes in blood brain permeability in the BBZDR/Wor rat an inbred rat strain model of type 2 diabetes (Tirabassi et al., 2004).

Methods

Animals

Male Bio-Breeding Zucker diabetic rats (BBZDR/Wor rats) (n=8) and age-matched non-diabetic BBDR littermates (n=8), were obtained from Biomere (Worcester, Mass.). The obese male BBZDR/Wor rat spontaneously develops type 2 diabetes at approximately 10 weeks of age (~100%) when fed standard rat chow. BBZDR/Wor diabetic rat displays all clinical symptoms typically associated with type 2 diabetes including dyslipidemia, hyperglycemia, insulin resistance, and hypertension (Tirabassi et al., 2004).

Rats were maintained on a 12 h:12 h light-dark cycle with a lights on at 07:00 h, allowed access to food and water ad libitum and were treated with ip injections of saline at indications of weight loss. All animal experiments were conducted in accordance with the Northeastern University Division of Laboratory Animal Medicine and Institutional Animal Care and Use Committee.

Access to rats was dependent upon the breeding schedule and resulting genotypes. Because of this, two separate imaging studies were run, each with four rats from each genotype, separated by six months.

Imaging

Studies were done on a Bruker Biospec 7.0T/20-cm USR horizontal magnet (Bruker, Billerica, Mass., USA) and a 20-G/cm magnetic field gradient insert (ID=12 cm) capable of a 120 μs rise time. Radio frequency signals were sent and received with a quadrature volume coil built into the rat restrainer (Animal Imaging Research, Holden, Mass.). All rats imaged under 1-2% isoflurane while keeping a respiratory rate of 40-50 breadths/min. At the beginning of each imaging session, a high-resolution anatomical data set was collected using the RARE pulse sequence with following parameters, 35 slice of 0.7 mm thickness; field of view [FOV] 3 cm; 256×256; repetition time [TR] 3900 msec; effective echo time [TE] 48 msec; NEX 3; 6 min 14 sec acquisition time.

Rats were imaged prior to and following an i.v. bolus of 6 mg/mL Fe of Ferumoxytol. The injected volume was tailored for each rat (assuming 7% blood by body weight) to produce a starting blood concentration of 200 μg/mL Fe (2× the clinical dose approved for use in humans). The QUTE-CE MRI image parameters of TE=13 TR=4 ms, and FA=20° utilized a high RF pulse bandwidth of 200 kHz. Therefore, the pulse duration was short (6.4 μs) compared to the T2 of the approximate ferumoxytol concentration (4.58 ms for 3.58 mM, i.e. 200 μg/mL to minimize signal blur and reduce the probability for a curved trajectory of the magnetization vector Mz. A 3×3×3 cm³ field-of-view was used with a matrix mesh size of 180×180×180 to produce 167 μm isotropic resolution.

Images were motion-corrected, aligned spatially, and resliced using MATLAB SPM12 toolbox developed at UCL (http://www.fil.ion.ucl.ac.uk/spm/). The pre-contrast UTE images were set as the baseline. For each rat in each imaging session, the voxel wise percentage change of signal intensity for each scan time point (post-con) was calculated as (post-contrast−postcontrast initial)/(postcontrast initial)*100%. A 173-region rat brain atlas (Ekam Solutions LLC, Boston, Mass., US) was fit to T2-weighted RARE anatomical data set for each rat data set taken at each imaging session, considering the variations in brain size and positions. The fitted atlas was transferred to UTE imaging. Once the images were co-registered to the atlas, custom MATLAB code was used to mask individual brain regions for ferumoxytol measurement.

Statistics

QUTE-CE time-variant curves were compared by two-way ANOVA with Tukey's post hoc test for simple effect comparison at each time point. Parameters extracted from fitting curves were compared using student's t-test. P value <0.05 was regarded as statistically significant.

Results

FIG. 6A provides images of rat brain regions with regions gray shaded which showed significantly greater BBB permeability in type 2 diabetic, BBZDR/Wor rats as compared to wild-type controls. Areas in white localized to the prefrontal ctx, midbrain and cerebellum were not significantly different. These areas in white are coalesced into 3D volumes and shown in FIG. 6B as shaded regions of a glass brain.

CONCLUSIONS

As demonstrated in this study with the BBZDR/Wor rats, a preclinical model of type 2 diabetes, this imaging technology could be used to evaluate vascular disruption from neurological dysfunction in disease.

REFERENCES CITED

Allen, C. L., and Bayraktutan, U. (2009) Antioxidants attenuate hyperglycaemia-mediated brain endothelial cell dysfunction and blood-brain barrier hyperpermeability. Diabetes, obesity & metabolism 11, 480-490.

Bremerich J, Bilecen D, Reimer P. MR angiography with blood pool contrast agents. European radiology 2007; 17(12): 3017-24.

Bogush, M., Heldt, N. A., and Persidsky, Y. (2017) Blood Brain Barrier Injury in Diabetes: Unrecognized Effects on Brain and Cognition. Journal of Neuroimmune Pharmacology: the official journal of the Society on Neuroimmune Pharmacology 12, 593-601.

De Beaumont L, Henry L C, Gosselin N. Long-term functional alterations in sports concussion. Neurosurgical focus 2012; 33(6): E8: 1-7.

Gardner R C, Yaffe K. Epidemiology of mild traumatic brain injury and neurodegenerative disease. Molecular and cellular neurosciences 2015; 66(Pt B): 75-80.

Gharagouzloo C A, McMahon P N, Sridhar S. Quantitative contrast-enhanced MM with superparamagnetic nanoparticles using ultrashort time-to-echo pulse sequences. Magn Reson Med 2015; 74(2): 431-41.

Gharagouzloo C A, Timms L, Qiao J, Fang Z, Nneji J, Pandya A, et al. Quantitative vascular neuroimaging of the rat brain using superparamagnetic nanoparticles: New insights on vascular organization and brain function. NeuroImage 2017; 163: 24-33.

Held F, Morris A W J, Pirici D, Niklass S, Sharp M M G, Garz C, et al. Vascular basement membrane alterations and beta-amyloid accumulations in an animal model of cerebral small vessel disease. Clin Sci (Lond) 2017; 131(10): 1001-13.

Heye A K, Culling R D, Valdes Hernandez Mdel C, Thrippleton M J, Wardlaw J M. Assessment of blood-brain barrier disruption using dynamic contrast-enhanced MM. A systematic review. NeuroImage Clinical 2014; 6: 262-74.

Iverson G L. Outcome from mild traumatic brain injury. Curr Opin Psychiatry 2005; 18(3): 301-17.

Jafari S, Etminan M, Aminzadeh F, Samii A. Head injury and risk of Parkinson disease: a systematic review and meta-analysis. Movement disorders: official journal of the Movement Disorder Society 2013; 28(9): 1222-9.

Kulkarni P, Morrison T R, Cai X, Iriah S, Simon N, Sabrick J, et al. Neuroradiological Changes Following Single or Repetitive Mild TBI. Frontiers in systems neuroscience 2019; 13: 34.

McKee A C, Cairns N J, Dickson D W, Folkerth R D, Keene C D, Litvan I, et al. The first NINDS/NIBIB consensus meeting to define neuropathological criteria for the diagnosis of chronic traumatic encephalopathy. Acta neuropathologica 2016; 131(1): 75-86.

Menon D K, Schwab K, Wright D W, Maas A I, Demographics, Clinical Assessment Working Group of the I, et al. Position statement: definition of traumatic brain injury. Archives of physical medicine and rehabilitation 2010; 91(11): 1637-40.

Muehe A M, Feng D, von Eyben R, Luna-Fineman S, Link M P, Muthig T, et al. Safety Report of Ferumoxytol for Magnetic Resonance Imaging in Children and Young Adults. Investigative radiology 2016; 51(4): 221-7.

Mychasiuk R, Hehar H, Candy S, Ma I, Esser M J. The direction of the acceleration and rotational forces associated with mild traumatic brain injury in rodents effect behavioural and molecular outcomes. Journal of neuroscience methods 2016; 257: 168-78.

Natarajan R, Northrop N, Yamamoto B. Fluorescein Isothiocyanate (FITC)-Dextran Extravasation as a Measure of Blood-Brain Barrier Permeability. Current protocols in neuroscience/editorial board, Jacqueline N Crawley [et al] 2017; 79: 9 58 1-9 15.

Palacios E M, Yuh E L, Chang Y S, Yue J K, Schnyer D M, Okonkwo D O, et al. Resting-State Functional Connectivity Alterations Associated with Six-Month Outcomes in Mild Traumatic Brain Injury. Journal of neurotrauma 2017; 34(8): 1546-57.

Pantoni L. Cerebral small vessel disease: from pathogenesis and clinical characteristics to therapeutic challenges. Lancet neurology 2010; 9(7): 689-701.

Pasquier, F., Boulogne, A., Leys, D., and Fontaine, P. (2006) Diabetes mellitus and dementia. Diabetes Metab 32, 403-414.

Plassman B L, Havlik R J, Steffens D C, Helms M J, Newman T N, Drosdick D, et al. Documented head injury in early adulthood and risk of Alzheimer's disease and other dementias. Neurology 2000; 55(8): 1158-66.

Prins M L, Alexander D, Giza C C, Hovda D A. Repeated mild traumatic brain injury: mechanisms of cerebral vulnerability. Journal of neurotrauma 2013; 30(1): 30-8.

Qin Y, Li G L, Xu X H, Sun Z Y, Gu J W, Gao F B. Brain structure alterations and cognitive impairment following repetitive mild head impact: An in vivo MRI and behavioral study in rat. Behav Brain Res 2018; 340: 41-8.

Raja R, Rosenberg G A, Caprihan A. MRI measurements of Blood-Brain Barrier function in dementia: A review of recent studies. Neuropharmacology 2018; 134(Pt B): 259-71.

Rajesh A, Cooke G E, Monti J M, Jahn A, Daugherty A M, Kramer A. Differences in Brain Architecture in Remote Mild Traumatic Brain Injury. Journal of neurotrauma 2017.

Schabel M C, Parker D L. Uncertainty and bias in contrast concentration measurements using spoiled gradient echo pulse sequences. Physics in medicine and biology 2008; 53(9): 2345-73.

Shlosberg D, Benifla M, Kaufer D, Friedman A. Blood-brain barrier breakdown as a therapeutic target in traumatic brain injury. Nature reviews Neurology 2010; 6(7): 393-403.

Starr, J. M., Wardlaw, J., Ferguson, K., MacLullich, A., Deary, I. J., and Marshall, I. (2003) Increased blood-brain barrier permeability in type II diabetes demonstrated by gadolinium magnetic resonance imaging. Journal of neurology, neurosurgery, and psychiatry 74, 70-76.

Tirabassi, R. S., Flanagan, J. F., Wu, T., Kislauskis, E. H., Birckbichler, P. J., and Guberski, D. L. (2004) The BBZDR/Wor rat model for investigating the complications of type 2 diabetes mellitus. ILAR J 45, 292-302.

Thrippleton M J, Backes W H, Sourbron S, Ingrisch M, van Osch M J P, Dichgans M, et al. Quantifying blood-brain barrier leakage in small vessel disease: Review and consensus recommendations. Alzheimers Dement 2019; 15(6): 840-58.

Viano D C, Hamberger A, Bolouri H, Saljo A. Concussion in professional football: animal model of brain injury—part 15. Neurosurgery 2009; 64(6): 1162-73; discussion 73.

Walker-Samuel S, Parker C C, Leach M O, Collins D J. Reproducibility of reference tissue quantification of dynamic contrast-enhanced data: comparison with a fixed vascular input function. Physics in medicine and biology 2007; 52(1): 75-89.

Wardlaw J M. Blood-brain barrier and cerebral small vessel disease. J Neurol Sci 2010; 299(1-2): 66-71.

Wardlaw J M, Smith E E, Biessels G J, Cordonnier C, Fazekas F, Frayne R, et al. Neuroimaging standards for research into small vessel disease and its contribution to ageing and neurodegeneration. Lancet neurology 2013; 12(8): 822-38.

Weil Z M, Gaier K R, Karelina K. Injury timing alters metabolic, inflammatory and functional outcomes following repeated mild traumatic brain injury. Neurobiol Dis 2014; 70: 108-16.

Yoshiyama Y, Uryu K, Higuchi M, Longhi L, Hoover R, Fujimoto S, et al. Enhanced neurofibrillary tangle formation, cerebral atrophy, and cognitive deficits induced by repetitive mild brain injury in a transgenic tauopathy mouse model. Journal of neurotrauma 2005; 22(10): 1134-41.

U.S. Patent Application Publication No. 2019/0246938, entitled "Quantitative Magnetic Resonance Imaging of the Vasculature"; incorporated by reference.

The teachings of the documents cited herein are hereby incorporated by reference.

EQUIVALENTS

The present technology (including present methods) is not limited to the particular embodiments described in this application, which are intended as individual illustrations of aspects of the present technology. Many modifications and variations of the present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, compounds, compositions, disease pathologies, or devices, which can, of course, vary. It is also to be understood that the terminology used herein is for the purpose of describing particular embodiments only, and is not intended to be limiting.

What is claimed is:

1. A method comprising:

quantifying a disruption of one or more endothelial walls in a region of interest of a subject, the quantifying comprising:

analyzing magnetic resonance imaging (MRI) data of an extravascular space of the region of interest, the MRI data of the extravascular space comprising first MRI data captured at a first time point and second MRI data captured at a second time point, the analyzing the MRI data comprising identifying a first signal intensity in the extravascular space for the first time point and a second signal intensity in the extravascular space for the second time point, the first time point and the second time point being after a paramagnetic or superparamagnetic blood pool contrast agent was introduced into vasculature of the region of interest of the subject, wherein each of the first signal intensity and the second signal intensity is obtained via an MRI device configured with a repetition time (TR) less than 10 ms and a time to echo (TE) less than 300μs;

calculating a change in signal intensity in the region of interest, the change in signal intensity being based on a difference between the first signal intensity and the second signal intensity; and evaluating the change in signal intensity to measure the disruption of the one or more endothelial walls within the region of interest, wherein the evaluating comprises identifying a disruption in the one or more endothelial walls in response to the change in signal intensity exceeding a predetermined threshold.

2. The method of claim 1, wherein each of the first signal intensity and the second signal intensity is obtained by applying a magnetic field to the region of interest; applying a radio frequency pulse sequence with a selected repetition time (TR) and a selected flip angle (FA) to excite protons in the region of interest, wherein the repetition time is less than about 10 ms, and the selected flip angle ranges from 10° to 30°; measuring a response signal during relaxation of the protons at a selected time-to-echo (TE) with magnetic field gradients activated to provide a $T_1$-weighted signal from the region of interest, wherein the time-to-echo is an ultra- short time-to-echo, or Zero TE (ZTE), less than 300 μs; and generating an image of the region of interest.

3. The method of claim 2, wherein each of the first signal intensity and the second signal intensity are representative of a concentration of the contrast agent in the region of interest.

4. The method of claim 1, further comprising setting the time to echo (TE) to less than 30 μs.

5. The method of claim 1, further comprising setting the repetition time to a value from 2 to 10 ms.

6. The method of claim 1, further comprising setting a flip angle to a value from 10° to 25°.

7. The method of claim 1, wherein the first signal intensity is obtained before presence of the contrast agent in a brain parenchyma and the second signal intensity is subsequently obtained after administration of the contrast agent.

8. The method of claim 1, wherein each of the first signal intensity and the second signal intensity is obtained on the region of interest at a time when the contrast agent has cleared from a subject's vascular system.

9. The method of claim 1, wherein the region of interest is the subject's entire brain.

10. The method of claim 1, wherein the contrast agent is ferumoxytol.

11. The method of claim 10, wherein ferumoxytol is administered in a dose to produce a starting blood concentration of between 20 and 200 μg/mL Fe.

12. The method of claim 10, wherein ferumoxytol is administered in a dose to produce a starting blood concentration of between 40 and 150 μg/mL Fe.

13. The method of claim 10, wherein ferumoxytol is administered at a dose of 200 mg to 510 mg elemental iron.

14. The method of claim 10, wherein ferumoxytol is administered at a dose of 2 to 14 mg Fe/kg body weight.

15. The method of claim 10, wherein ferumoxytol is administered at a dose of 3 to 4 mg Fe/kg body weight.

16. The method of claim 1, wherein the subject is a human.

17. The method of claim 1, wherein the subject has traumatic brain injury, type 2 diabetes, stroke, or a CNS disorder.

18. The method of claim 17, wherein the subject has a CNS disorder; and the CNS disorder is amyotrophic lateral sclerosis, frontotemporal dementia, Huntington's disease, Alzheimer's disease or related dementia, or Parkinson's disease.

19. The method of claim 1, wherein the subject has minor cognitive impairment.

20. A computing system comprising:

one or more processors; and storage encoded with instructions that, when executed by the one or more processors, cause the one or more processors to perform a method comprising:

quantifying a disruption of one or more endothelial walls in a region of interest of a subject, the quantifying comprising:

analyzing magnetic resonance imaging (MRI) data of an extravascular space of the region of interest, the MRI data of the extravascular space comprising, first MRI data captured at a first time point and second MRI data captured at a second time point, the analyzing the MRI data comprising identifying a first signal intensity in the extravascular space for the first time point and a second signal intensity in the extravascular space for the second time point, the first time point and the second time point being after a paramagnetic or superparamagnetic blood pool contrast agent was introduced into vasculature of the region of interest of the subject, wherein each of the first signal intensity and the second signal intensity is obtained via an MRI device configured with a repetition time (TR) less than 10 ms and a time to echo (TE) less than 300 μs;

calculating a change in signal intensity in the region of interest, the change in signal intensity being based on a difference between the first signal intensity and the second signal intensity; and evaluating the change in signal intensity to measure the disruption of the one or more endothelial walls within the region of interest, wherein the evaluating comprises identifying a disruption in the one or more endothelial walls in response to the change in signal intensity exceeding a predetermined threshold.

21. At least one nontransitory computer-readable storage medium having encoded thereon instructions that, when executed by at least one processor, cause the at least one processor to carry out a method comprising:

quantifying a disruption of one or more endothelial walls in a region of interest of a subject, the quantifying comprising:

analyzing magnetic resonance imaging (MRI) data of an extravascular space of the region of interest, the MRI data of the extravascular space comprising first MRI data captured at a first time point and second MRI data captured at a second time point, the analyzing the MRI data comprising identifying a first signal intensity in the extravascular space for the first time point and a second signal intensity in the extravascular space for the second time point, the first time point and the second time point being after a paramagnetic or superparamagnetic blood pool contrast agent was introduced into vasculature of the region of interest of the subject, wherein each of the first signal intensity and the second signal intensity is obtained via an MRI device configured with a repetition time (TR) less than 10 ms and a time to echo (TE) less than 300 μs;

calculating a change in signal intensity in the region of interest, the change in signal intensity being based on a difference between the first signal intensity and the second signal intensity; and evaluating the change in signal intensity to measure the disruption of the one or more endothelial walls within the region of interest, wherein the evaluating comprises identifying a disruption in the one or more endothelial walls in response to the change in signal intensity exceeding a predetermined threshold.

* * * * *